US010316287B2

(12) United States Patent
Gundry et al.

(10) Patent No.: US 10,316,287 B2
(45) Date of Patent: Jun. 11, 2019

(54) METHODS FOR SELECTIVE INHIBITION OF PLURIPOTENT STEM CELLS

(71) Applicant: THE MEDICAL COLLEGE OF WISCONSIN, INC., Milwaukee, WI (US)

(72) Inventors: Rebekah L. Gundry, Milwaukee, WI (US); Kenneth R. Boheler, Hong Kong (CN); Erin M. Kropp, Milwaukee, WI (US)

(73) Assignee: The Medical College of Wisconsin, Inc., Milwaukee, WI (US)

( * ) Notice: Subject to any disclaimer, the term of this patent is extended or adjusted under 35 U.S.C. 154(b) by 28 days.

(21) Appl. No.: 15/112,923

(22) PCT Filed: Jan. 21, 2015

(86) PCT No.: PCT/US2015/012218
§ 371 (c)(1),
(2) Date: Jul. 20, 2016

(87) PCT Pub. No.: WO2015/112581
PCT Pub. Date: Jul. 30, 2015

(65) Prior Publication Data
US 2016/0340642 A1 Nov. 24, 2016

Related U.S. Application Data

(60) Provisional application No. 61/929,659, filed on Jan. 21, 2014.

(51) Int. Cl.
*C12N 5/00* (2006.01)
*C12N 5/02* (2006.01)
*C12N 5/0735* (2010.01)
*C12N 5/074* (2010.01)
*A61K 35/545* (2015.01)
*C12N 5/077* (2010.01)

(52) U.S. Cl.
CPC .......... *C12N 5/0081* (2013.01); *A61K 35/545* (2013.01); *C12N 5/0606* (2013.01); *C12N 5/0657* (2013.01); *C12N 5/0696* (2013.01); *C12N 2500/38* (2013.01); *C12N 2501/72* (2013.01); *C12N 2501/724* (2013.01); *C12N 2506/45* (2013.01)

(58) Field of Classification Search
CPC .................................................. C12N 5/0081
See application file for complete search history.

(56) References Cited

U.S. PATENT DOCUMENTS

2013/0280802 A1  10/2013  Schulz et al.

FOREIGN PATENT DOCUMENTS

| WO | 2006115080 A1 | 11/2006 |
| WO | 2009100116 A1 | 8/2009 |
| WO | 2010002465 A2 | 1/2010 |
| WO | 2012042519 A1 | 4/2012 |
| WO | 2012078153 | 6/2012 |
| WO | 2012100223 A1 | 7/2012 |
| WO | 2013078392 A1 | 5/2013 |
| WO | 2013148994 A1 | 10/2013 |
| WO | 2013175474 A2 | 11/2013 |

OTHER PUBLICATIONS

Lee, 2013, PNAS, E3281-E3290.*
Zhang (2012, Cell Stem Cell, 11:589-595).*
Okamura (2012, Jourmal of Thoracic Oncology, 7:49-56).*
Son (2013, 2013, Stem Cells, 34:1121-1135).*
Chan (2011, Science Translational Medicine, 3:1-9).*
Kropp (2015, Stem Cells Translational Medicine, 4:483-493).*
International Search Report and Written Opinion issued in corresponding International Application No. PCT/US2015/012218, dated Mar. 26, 2015, 21 pages.
Adams et al., ACS Chem. Biol. 9(10):2247-2254 (2014).
Altman, B.J. and J.C. Rathmell, Metabolic stress in autophagy and cell death pathways. Cold Spring Harb Perspect Biol, 2012. 4(9): p. a008763.
Ben-David, U., N. Nudel, and N. Benvenisty, Immunologic and chemical targeting of the tight-junction protein Claudin-6 eliminates tumorigenic human pluripotent stem cells. Nat Commun, 2013. 4: p. 1992.
Ben-David, Uri et al., "Selective Elimination of Human Pluripotent Stem Cells by an Oleate Synthesis Inhibitor Discovered in a High-Throughput Screen," Cell Stem Cell, vol. 12, No. 2, Feb. 1, 2013, pp. 167-179.
Ben-David, Uri et al., "Chemical ablation of tumor-initiating human pluripotent stem cells;" Nature Protocols, vol. 9, No. 3, Mar. 1, 2014, pp. 729-740.
Ben-David, Uri et al., "Brief Reports: Controlling the Survival of Human Pluripotent Stem Cells by Small Molecule-Based Targeting of Topoisomerase IIAlpha," Stem Cells, vol. 33, No. 3, Mar. 1, 2015, pp. 1013-1019.
Bhattacharya, S., et al., High efficiency differentiation of human pluripotent stem cells to cardiomyocytes and characterization by flow cytometly. J Vis Exp, 2014(91): p. 52010.
Bieberich E et al., "Selective apoptosis of pluripotent mouse and human stem cells by nobel ceramide analogues prevents teratoma formation and enriches for neural precursors in ES cell-derived neural transplants," The Journal of Cell Biology: JCB, The Rockefeller University Press, US, vol. 167, No. 4, Nov. 22, 2004, pp. 723-734.
Bock et al., Cell 144:439-452 (2011).
Boheler, K.R., et al., A human pluripotent stem cell surface N-glycoproteome resource reveals markers, extracellular epitopes, and drug targets. Stem Cell Reports, 2014. 3(1): p 185-203.

(Continued)

*Primary Examiner* — Valarie E Bertoglio
(74) *Attorney, Agent, or Firm* — Quarles & Brady LLP

(57) ABSTRACT

Provided herein are methods of reducing or eliminating undifferentiated pluripotent stem cells, where the methods comprise contacting an effective amount of a compound to a heterogeneous cell population or sample comprising or suspected of comprising differentiated cell types and undifferentiated pluripotent stem cells, whereby the contacting selectively reduces or eliminates undifferentiated pluripotent stem cells from the cell population or sample. Also provided are methods for obtaining a population of stem cell-derived cell types substantially free of undifferentiated pluripotent stem cells as well as isolated populations of such of stem cell-derived cell types.

5 Claims, 45 Drawing Sheets

(56) References Cited

OTHER PUBLICATIONS

Broniowska, K.A., et al., Effect of nitric oxide on naphthoquinone toxicity in endothelial cells: role of bioenergetic dysfunction and poly (ADP-ribose) polymerase activation. Biochemistry, 2013. 52(25): p. 4364-4372.
Busso et al., Plos One 3:e2267 (2008), p. 1-10.
Cao, F., et al., Molecular imaging of embryonic stem cell misbehavior and suicide gene ablation. Cloning Stem Cells, 2007. 9(1): p. 107-117.
Chong, 1.1, et al., Human embryonic-stem-cell-derived cardiomyocytes regenerate non-human primate hearts. Nature, 2014, 17 pages.
Choo, A B et al., "Selection against undifferentiated human embryonic stem cells by a cytotoxic antibody recognizing podocalyxin-like protein-1," Stem Cells, Alphamed Press, Dayton, OH, US, vol. 26, No. 6, Jun. 1, 2008, pp. 1454-1463.
Coloff, J.L., et al., Akt requires glucose metabolism to suppress puma expression and prevent apoptosis of leukemic T cells. J Biol Chem, 2011.286(7): p. 5921-33.
Cui, L., et al., WNT signaling detennines tumorigenicity andfimction ofESC-derived retinal progenitors. J Clin Invest, 2013. 123(4): p. 1647-1661.
Dabir, Deepa V et al., "A Small Molecule Inhibitor of Redox-Regulated Protein Translocation into Mitochondria," Developmental Cell, Cell Press, US, vol. 25, No. 1, Apr. 15, 2013, pp. 81-92.
Doi, D., et al., Prolonged maturation culture favors a reduction in the tumorigenicity and the dopaminergic function of human ESC-derived neural cells in a primate model of Parkinson's disease. Stem Cells, 2012. 30(5): p. 935-945.
Dubois, Nicole C et al., "SIRPA is a specific cell-surface marker for isolating cardiomyocytes derived from human pluripotent stem cells," Nature Biotechnology, Nature Publishing Group, US, vol. 29, No. 11, Nov. 1, 2011, pp. 1011-1018.
Ebert, A.D., P. Liang, and J.C. Wu, Induced pluripotent stem cells as a disease modeling and drug screening platform. J Cardiovasc Pharmacol, 2012. 60(4): p. 408-416.
Feng et al., Stem Cells 28:704-712 (2010).
Folmes, C.D., et al., Energy metabolism plasticity enables sternness programs. Ann NY Acad Sci, 2012. 1254: p. 82-89.
Gore et al., Nature 471:63-67 (2011).
Grskovic, M., et al., Induced pluripotent stem cells—opportunitiesfor disease modelling and drug discovery. Nat Rev Drug Discov, 2011. 10(12): p. 915-929.
Hattori, Fumiyuki et al., "Nongenetic method for purifying stem cell-derived cardiomyocytes," Nature Methods, vol. 7, No. 1, Jan. 1, 2010, pp. 61-66.
Hentze, H., et al., Teratoma formation by human emblyonic stem cells: evaluation of essential parameters for future safety studies. Stem Cell Res, 2009. 2(3): p. 198-210.
Khan, P., et al., Luminol-Based Chemiluminescent Signals: Clinical and Non-clinical Application and Future Uses. Appl Biochem Biotechnol, 2014. 173(2): p. 333-355.
Kroon, E., et al., Pancreatic endoderm derived from human embryonic stem cells generates glucose-responsive insulin-secreting cells in vivo. Nat Biotechnol, 2008. 26(4): p. 443-452.
Lee, A.S., et al., Tumorigenicity as a clinical hurdle for pluripotent stem cell therapies. Nat Med, 2013. 19(8): p. 998-1004.
Liu, Y. et al., "A Small-Molecule Inhibitor of Glucose Transporter 1 Downregulates Glycolysis, Induces Cell-Cycle Arrest, and Inhibits Cancer Cell Growth In Vitro and In Vivo," Molecular Cancer Therapeutics, vol. 11, No. 8, Aug. 1, 2012, pp. 1672-1682.
Maherali and Hochedlinger, Cell Stem Cell 3:595-605 (2008).
Mallanna, S.K. and S.A. Duncan, Differentiation of hepatocytes from pluripotent stem cells. Curr Protoc Stem Cell Biol, 2013. 26: 1G.4.1-1G4.13, 15 page.
Meares, G.P., et al., AMP-activated protein kinase attenuates nitric oxide-induced β-cell death. J Biol Chem, 2010. 285(5): p. 3191-3200.
Muller et al., Nat. Methods 8:315-317 (2011).
O'Connor, M.D., M.D. Kardel, and C.J. Eaves, Functional assays for human embryonic stem cell pluripotency. Methods Mol Biol, 2011. 690: p. 67-80.
Rao, S., et al., Differential roles of Sall4 isoforms in embryonic stem cell pluripotency. Mol Cell Biol, 2010. 30(22): p. 5364-5380.
Repetto, G., A. del Peso, and J.L. Zurita, Neutral red uptake assay for the estimation of cell viability/cytotoxicity. Nat Protoc, 2008. 3(7): p. 1125-1131.
Robinton and Daley, Nature 481:295-305 (2012).
Rong, Z., et al., A scalable approach to prevent teratoma formation of human embryonic stem cells. J Biol Chem, 2012. 287(39): p. 32338-32345.
Schriebl, Kornelia et al., "Selective Removal of Undifferentiated Human Embryonic Stem Cells Using Magnetic Activated Cell Sorting Followed by a Cytotoxic Antibody," Tissue Engineerinf Part A, Jan. 4, 2012, pp. 899-909.
Shi, Y., et al., Human cerebral cortex development from pluripotent stem cells to fimctional excitatory synapses. Nat Neurosci, 2012. 15(3): p. 477-86, SI.
Takahashi, K and S. Yamanaka, Induced pluripotent stem cells in medicine and biology. Development, 2013. 140 (12): p. 2457-2461.
Tan, Heng Liang et al., "mAb 84, a Cytotoxic Antibody that Kills Undifferentiated Human Embryonic Stem Cells via Oncosis," Stem Cells, Alphamed Press, Dayton, OH, US, vol. 27, No. 8, Aug. 1, 2009, pp. 1792-1801.
Tang, C., et al., An antibody against SSEA-5 glycan on human pluripotent stem cells enables removal of teratoma-forming cells. Nat Biotechnol, 2011. 29(9): p. 829-834.
Thomson, J.A., et al., Embryonic stem cell lines derived from human blastocysts. Science, 1998. 282(5391): p. 1145-1147.
Tohyama, Shugo et al., "Distinct Metabolic Flow Enables Large-Scale Purification of Mouse and Human Pluripotent Stem Cell-Derived Cardiomyocytes," Cell Stem Cell, vol. 12, No. 1, Jan. 1, 2013, pp. 127-137.
Tomizama, Minoru et al., "Survival of Primary Human Hepatocytes and Death of Induced Pluripotent Stem Cells in Media Lacking Glucose and Arginine," PLoS One, vol. 8, No. 8, Aug. 14, 2013, p. e71897, 10 pages.
Von Heideman et al., Cancer Chemother. Pharmacol. 65(6):1165-1172 (2010).
Watson et al., Molecular and Cellular Biol. 29(21): 5872-5888 (2009).
Yu, J., et al., Human induced pluripotent stem cells free of vector and transgene sequences. Science, 2009. 324 (5928): p. 797-801.
Zhang et al., Teratoma formation: A tool for monitoring pluripotency in stem cell research, in Stem Book 2008, p. 1-14.
Zhang, J., et al., Measuring energy metabolism in cultured cells, including human pluripotent stem cells and differentiated cells. Nat Protoc, 2012. 7(6): p. 1068-1085.
Zhao, Y., et al., Glucose Metabolism Attenuates p53 and Puma-dependent Cell Death upon Growth Factor Deprivation. J Biol Chem, 2008. 283(52): p. 36344-36353.
Ziegler, Eur. J. Biochem. 267:1550-1564 (2000).
Kropp, Erin M. et al., "Inhibition of an NAD+ Salvage Pathway Provides Efficient and Selective Toxicity to Human Pluripotent Stem Cells," Stem Cells Translational Medicine, AlphaMed Press 2015; 4: 483-493.
Amit, M. and J. Itskovitz-Eldor, Morphology of Human Embryonic and Induced Pluripotent Stem Cell Colonies Cultured with Feeders, in Atlas of Human Pluripotent Stem Cells, M. Amit and J. Itskovitz-Eldor, Editors. 2012, Humana Press. p. 15-39.
Carrasco, R.A., N.B. Stamm, and B.K. Patel, One-step cellular caspase-3/7 assay. Biotechniques, 2003. 34(5): p. 1064-7.
Defrancesco, L., Fits and starts for Geron. Nat Biotechnol, 2009. 27(877).
Dragovich, P.S., et al., Fragment-based design of 3-aminopyridine-derived amides as potent inhibitors ofhwnan nicotina,nide phosphoribosyltransferase (NAA,,fPT). Bioorg Med Chem Lett, 2014. 24(3): p. 954-62.
Holen et al., Invest New Drugs 26(1):45-51 (2008).

(56) References Cited

OTHER PUBLICATIONS

Kuo, Tink-Fanf et al., "Selective Elimination of Human Pluripotent Stem Cells by a Marine National Product Derivative," Jounal of the American Cheminal Society, vol. 136, No. 28, Jul. 16, 2014, pp. 9798-9801.

Lawrenz, B., et al., Highly sensitive biosafety model for stem-cell-derived grafts. Cytotherapy, 2004. 6(3): p. 212-22.

Matsuura, Katsuhisa et al., "Elimination of Remaining Undifferentiated Induced Pluripotent Stem Cells in the Process of Human Cardiac Cell Sheet Fabrication Using a Methionine-Free Culture Condition," Tissue Engineering Part C: Mathods, vol. 21, No. 3, Mar. 1, 2015, pp. 330-338.

Wesselschmidt, R.L., Methods Mol Biol. 767:231-41 (2011).

Yamamoto, N., et al., Measurement of glucose uptake in cultured cells. Curr Protoc Pharmacol, 2011. Chapter 12: p. Unit 12 14 1-22.

Zheng et al., Bioorg Med Chem Lett. 23:5488-5497 (2013).

Zheng et al., J Med Chem. 56:6413-6433 (2013).

Obrien et al. "Supplementation of nicotinic acid with NAMPT inhibitors results in loss of in vivo efficacy in NAPRT1-deficient tumor models," Neoplasia, 15(12), 2013, 1314-1329.

\* cited by examiner

E   1.5e5 cells/cm² plated; treated 24 h post-plating
(sub-confluent)

1.5e5 cells/cm² plated; treated 96 h post-plating
(confluent)

7.5e5 cells/cm² plated; treated 24 h post-plating
(confluent)

D

F

B

METHODS FOR SELECTIVE INHIBITION OF PLURIPOTENT STEM CELLS

CROSS-REFERENCE TO RELATED APPLICATIONS

This application represents the U.S. National Stage of International Application No. PCT/US2015/012218, filed Jan. 21, 2015 which claims the benefit of U.S. Provisional Application No. 61/929,659, filed Jan. 21, 2014, which is incorporated by reference as if set forth in its entirety.

STATEMENT REGARDING FEDERALLY FUNDED RESEARCH OR DEVELOPMENT

This invention was made with government support under Grant No. 4R00HL094708-03, awarded by the National Heart, Lung, and Blood Institute and the National Institutes of Health. The government has certain rights in the invention.

BACKGROUND

Pluripotent stem cells, which include induced pluripotent stem cells (iPSCs) and embryonic stem cells (ESCs), are characterized by a capacity for self-renewal and an ability to differentiate into any functional cell in the body. Thus, pluripotent stem cells are valuable sources of differentiated somatic cell types for research and clinical applications. The advent of human iPSCs (hiPSCs), derived from somatic cells by the exogenous expression of defined transcription factors, has overcome ethical issues associated with human ESCs (hESCs) and, when derived from the patient, may avoid immunological complications. While promising, significant limitations to the therapeutic use of hiPSCs remain unresolved. These include interline variations ranging from inconsistent transcription factor expression and differential DNA methylation to sporadic point mutations and chromosomal defects that affect in vitro differentiation, tumorigenicity, and potential clinical applications (Lee et al., *Nature Med.* 19(8): p. 998-1004 (2013); Robinton and Daley, *Nature* 481:295-305 (2012); Feng et al., *Stem Cells* 28:704-712 (2010); Gore et al., *Nature* 471:63-67 (2011)). Moreover, current tests of hiPSC potency rely on extensive in vitro differentiation tests, in vivo teratoma assays in rodents (Robinton and Daley, *Nature* 481, 295-305 (2012); Maherali and Hochedlinger, *Cell Stem Cell* 3:595-605 (2008)) or bioinformatic and gene expression assays (Bock et al., *Cell* 144:439-452 (2011); Muller et al., *Nat. Methods* 8:315-317 (2011)) which cannot be practically implemented into high-throughput hiPSC line generation designed to limit interline variability.

SUMMARY OF THE INVENTION

In one aspect, the present invention provides a method of reducing or eliminating undifferentiated pluripotent stem cells. In one embodiment, the method comprises contacting an effective amount of a compound to a heterogeneous cell population or sample comprising or suspected of comprising differentiated cell types and undifferentiated pluripotent stem cells, whereby the contacting selectively reduces or eliminates undifferentiated pluripotent stem cells from the cell population or sample. The compound can be STF-31, FK866, or other inhibitor of nicotinamide phosphoribosyl-transferase (NAMPT). The effective amount can be an amount between about 0.1 µM and about 100 µM.

In a further aspect, the present invention provides a method of obtaining a population of stem cell-derived cell types substantially free of undifferentiated pluripotent stem cells. In one embodiment, the method comprises (a) inducing undifferentiated pluripotent stem cells to differentiate or partially differentiate into one or more stem cell-derived cell types; (b) contacting an effective amount of a compound to the induced cell population, whereby the contacting selectively reduces or eliminates undifferentiated pluripotent stem cells from the induced cell population; and (c) isolating the contacted cells to obtain a population of one or more stem cell-derived cell types, wherein the population is substantially free of undifferentiated pluripotent stem cells. The compound can be STF-31. The effective amount can be an amount between about 0.1 µM and about 100 µM. In some cases, the effective amount is about 2.5 µM. The one or more stem cell-derived cell types can be a cardiomyocyte, neural progenitor, neuron, retinal pigmented epithelial cell, liver cell, or mesenchymal stem cell.

In some embodiments, the method can further comprise expanding the isolated stem cell-derived cell types as single cell clones.

In another aspect, the present invention provides a population of stem cell-derived cell types substantially free of undifferentiated pluripotent stem cells obtained by a method provided herein.

These and other features, aspects, and advantages of the present invention will become better understood from the description that follows. In the description, reference is made to the accompanying drawings, which form a part hereof and in which there is shown by way of illustration, not limitation, embodiments of the invention. The description of preferred embodiments is not intended to limit the invention to cover all modifications, equivalents and alternatives. Reference should therefore be made to the claims recited herein for interpreting the scope of the invention.

BRIEF DESCRIPTION OF THE DRAWINGS

(FIGS. 7D-E) Densitometry for immunoblotting of p-AMPK, cleaved caspase-3, and cleaved caspase-9 in sub-confluent cells corresponding to blots in FIG. 3D. (D) Densitometry for 6-36 hour glucose deprivation in hiPSC (N=3). (E) Densitometry for 2.5 µM STF-31 and 30 µM WZB117 6-36 hour treatment (N=3).

DETAILED DESCRIPTION OF THE INVENTION

Figure 1:
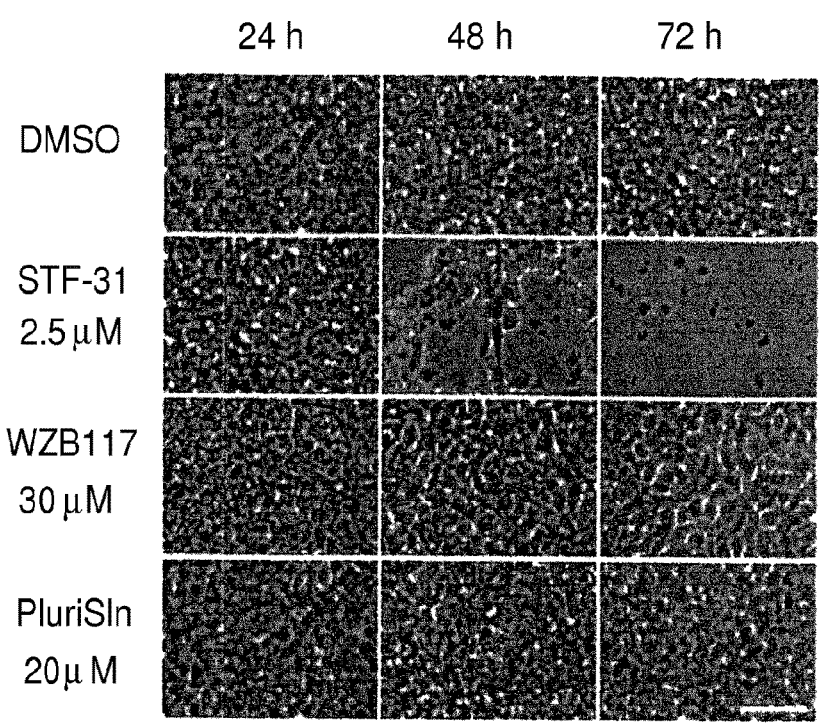
FIG. 1 presents data collected for human pluripotent stem cells (hPSCs) treated with small molecules. (A) Representative bright field images of confluent human induced pluripotent stem cells (hiPSCs) (DF6-9-9T) after treatment with 2.5 µM STF-31, 30 µM WZB117, and 20 µM PluriSIn for 24-72 hours. Scale bar=50 µm. (B) Cell viability as measured by SYTOX green assay in hiPSC treated with 20 µM PluriSIn, 30 µM WZB117, and 2.5 µM STF-31 (N=3). (C) Representative images of live (calcein AM-green)/dead staining (ethidium homodimer 1-red) in hiPSC after treatment with 20 µM PluriSIn, 30 µM WZB117, and 2.5 µM STF-31. Scale bar=100 µm. (D) Titration of STF-31 for 24-72 hours in confluent hiPSC determined by neutral red assay (N=3). (E) Cell viability of varying densities of hiPSC after treatment with 20 µM PluriSIn, 30 µM WZB117, and 2.5 µM STF-31 determined by neutral red assay (N=3). Representative images of cell morphology and density at 24 hours and 96 hour post-plating are coupled with respective bar graphs. Scale bar=200 µm. (F) Percent of live hiPSC in each phase of the cell cycle at 24-96 h post-plating (N=3). Schematic and results of colony forming assay where cells were passaged (G) or washed (H) prior to continued culture for 6 days prior to alkaline phosphatase staining. Arrows indicate individual colonies. Bar graphs representing average number of colonies per plate for each treatment scheme are shown (N=3). Data are represented as mean±SEM. * $p \leq 0.05$,  $p \leq 0.01$, * $p \leq 0.001$ compared to DMSO control.
Figure 1:
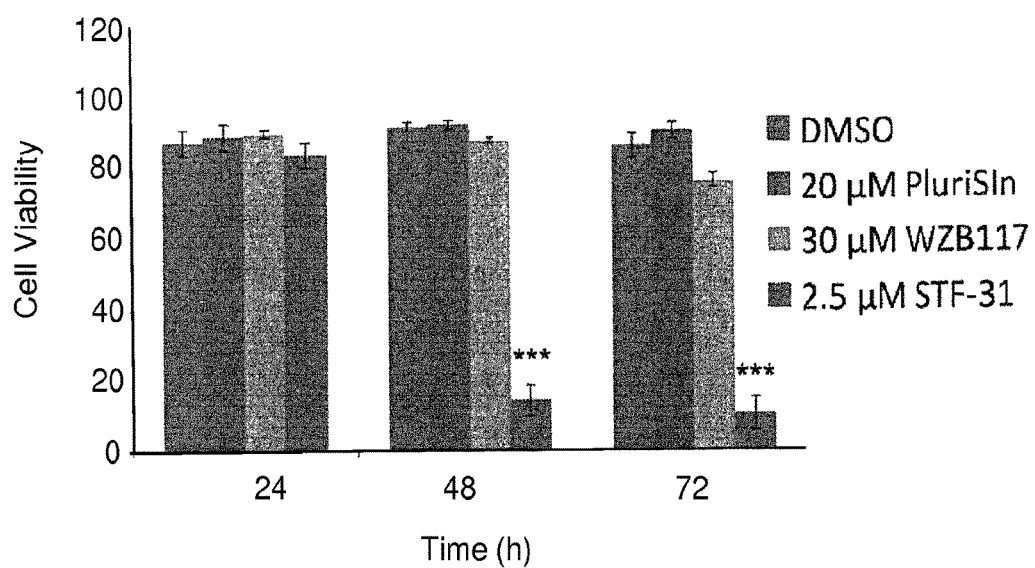
Figure 1:
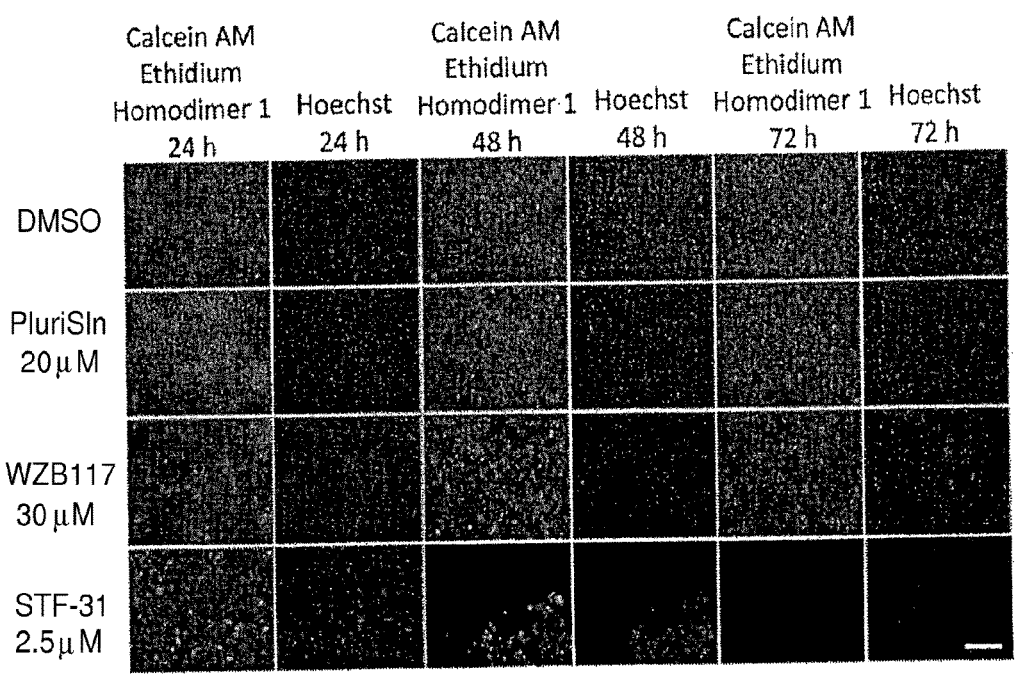
Figure 1:
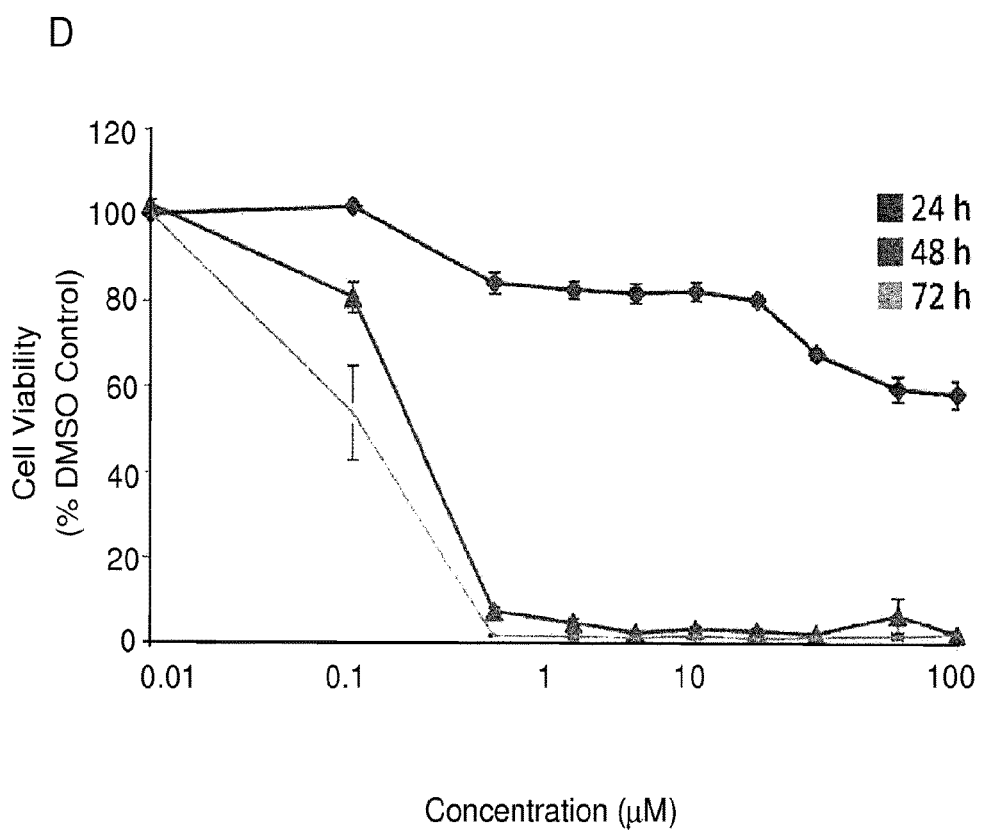
Figure 1:
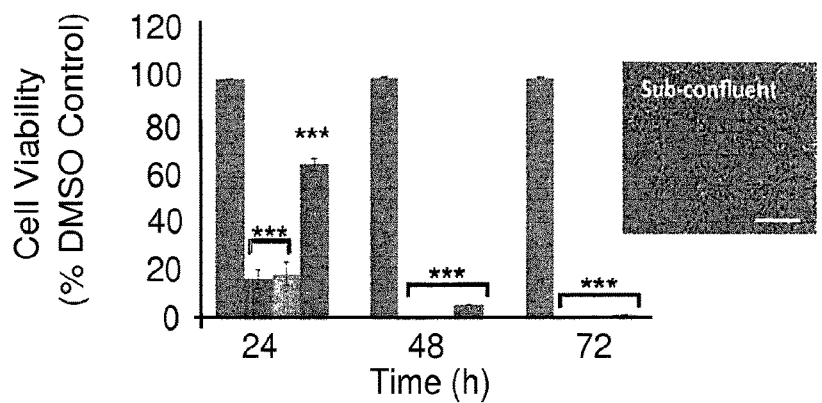
Figure 1:
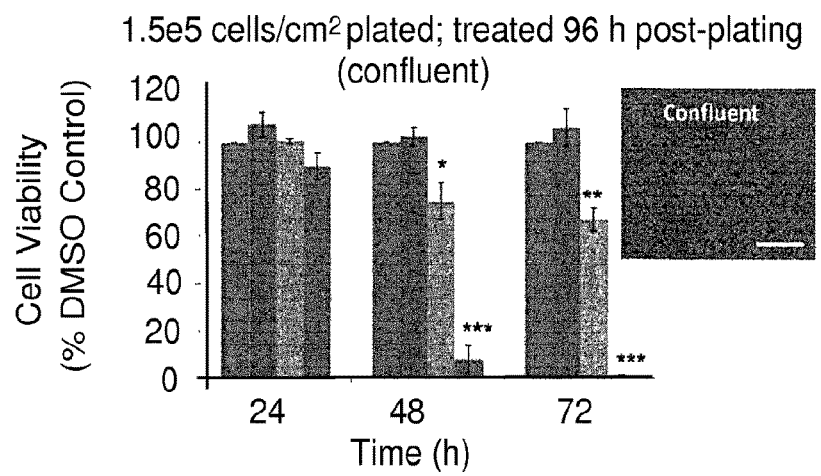
Figure 1:
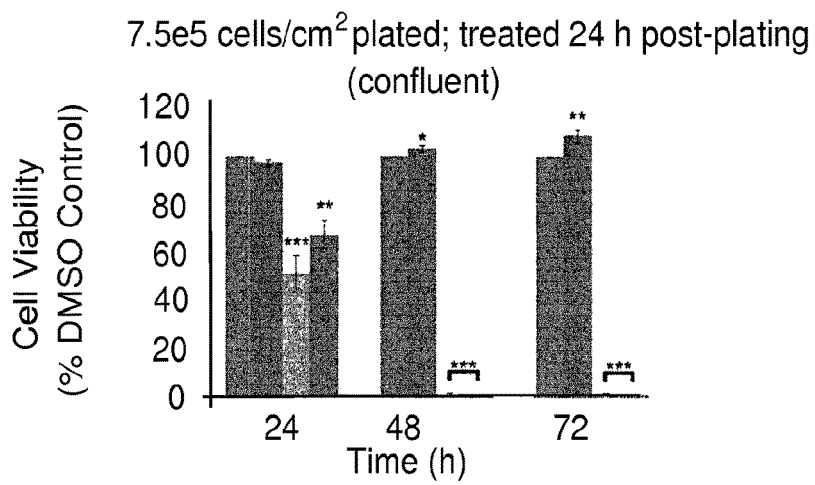
Figure 1:
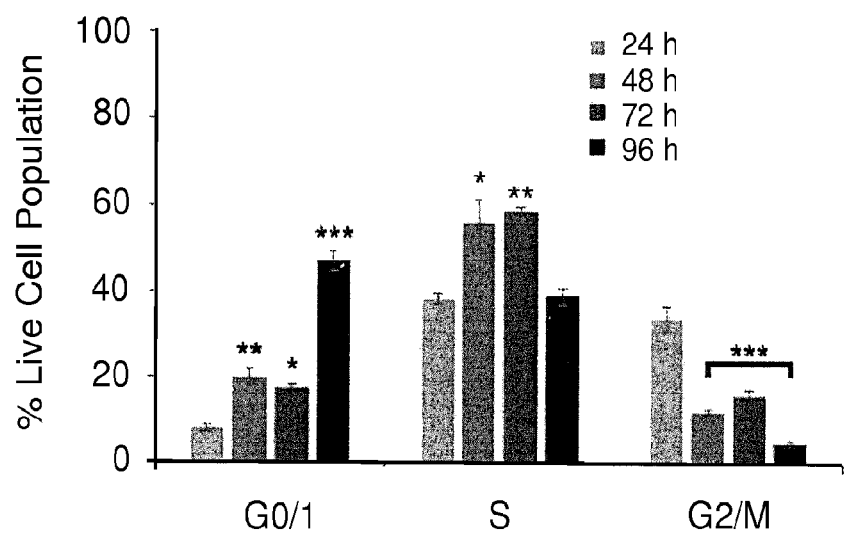
Figure 1:
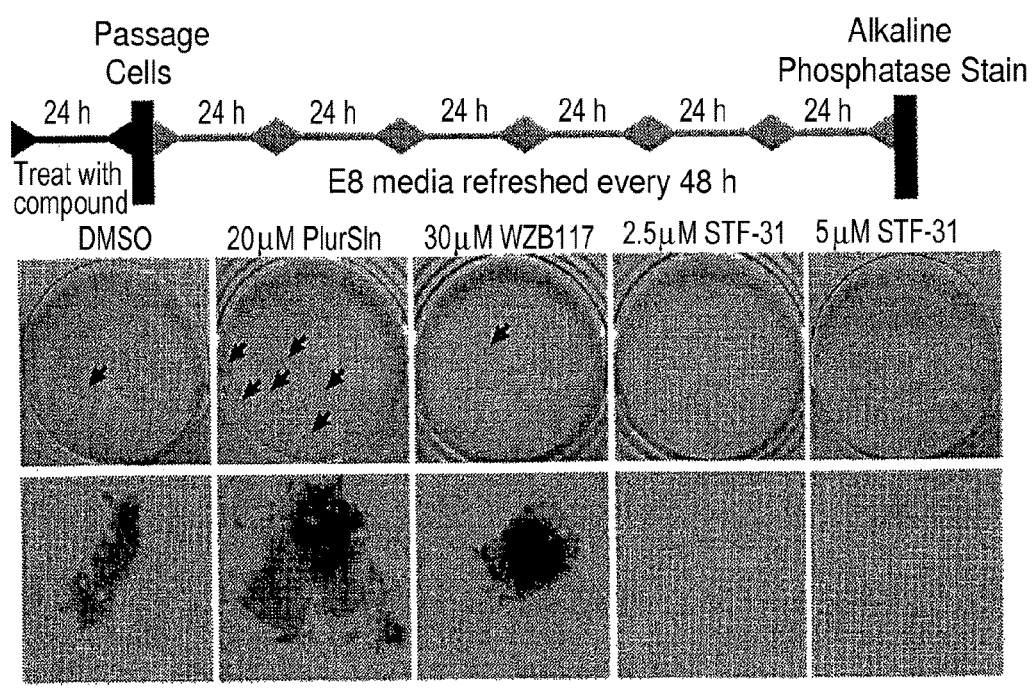
Figure 1:
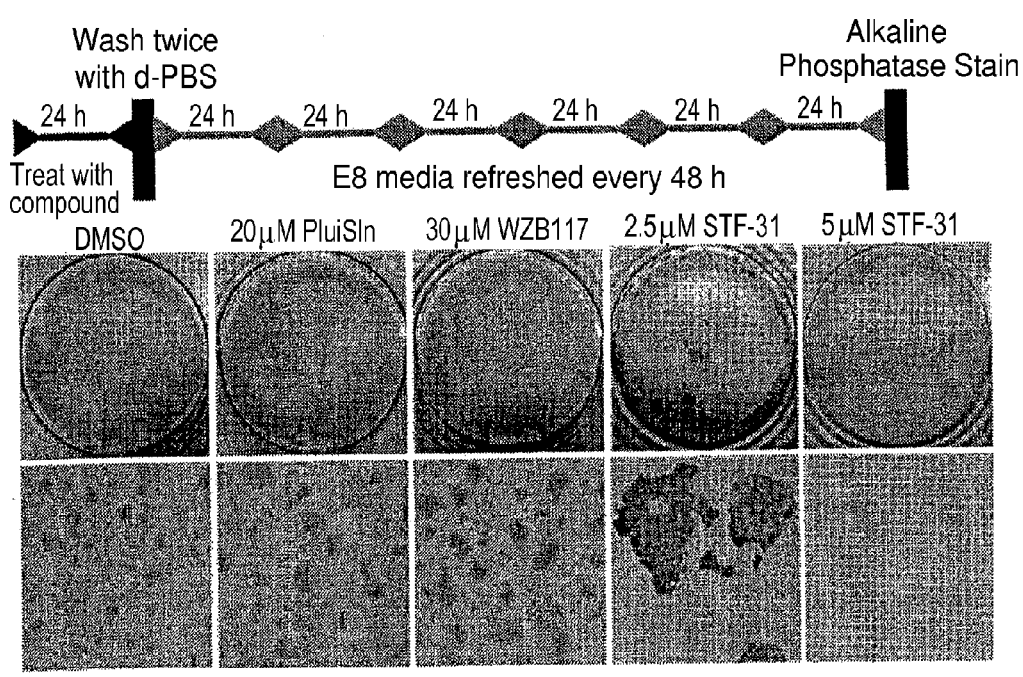

All publications, including but not limited to patents and patent applications, cited in this specification are herein incorporated by reference as though fully set forth in the present application.

The invention described herein is based, at least in part, on the Inventors' discovery that pluripotent stem cells can be selectively eliminated from a mixed population of differentiated and undifferentiated pluripotent cells. Terminally differentiated adult cells and partially differentiated ESCs and iPSCs generally rely on oxidative phosphorylation for cellular metabolism and growth, whereas undifferentiated ESCs and iPSCs are glycolysis-dependent and express several genes that encode various glucose transporter proteins for mediating glucose uptake. Using microarrays and proteomics, the Inventors identified a discrepancy in the correlation between transcription and cell surface localization of several glucose transporter proteins (e.g., GLUT1, GLUT3, and GLUT4). While WZB117 eliminates hPSC through inhibition of GLUT1, the Inventors discovered that STF-31, which was previously considered to be a GLUT1 inhibitor, does not function in this manner and, instead, removes hPSC through inhibition of the nicotinamide adenine dinucleotide ($NAD^+$) salvage pathway. These discoveries are consistent with and supported by two subsequent reports. Adams et al., *ACS Chem. Biol.* 9(10):2247-2254 (2014); Dragovich et al., *Bioorg Med Chem Lett* 24:954-962 (2014). Based on these findings, we developed a novel strategy for using STF-31 to effectively eliminate human pluripotent stem cells across a range of culture conditions by a process that spares differentiated progeny. These results provide an important advancement towards the development of clinically safe hPSC-derived progeny for human stem cell based therapies.

Accordingly, provided herein are methods for eliminating pluripotent stem cells from mixed cell populations of differentiated cells. In a first aspect, the present invention provides methods for obtaining a cell population devoid of undifferentiated pluripotent cells. In particular, the invention described herein provides methods for obtaining populations of cells differentiated from pluripotent stem cells, where the populations are free or substantially free of undifferentiated and potentially tumorigenic pluripotent stem cells. Methods of the present invention include methods of reducing or eliminating such undifferentiated pluripotent stem cells from a cell population comprising differentiated and undifferentiated cell types. As used herein, the terms "free" and "substantially free" with regard to cell populations refer to cell populations that comprise fewer than about 5%, preferably fewer than about 1%, and more preferably fewer than about 0.1% (e.g., fewer than 5%, 4%, 3%, 2%, 1%, 0.5%, 0.1%, 0.05%, 0.01%, 0%) undifferentiated pluripotent stem cells per unit volume, as compared to the cell population from which it was obtained. Cell populations obtained according to a method provided herein can be assessed and identified as free or substantially free of undifferentiated pluripotent stem cells using, for example, visual examinations (e.g., visually identifying residual undifferentiated pluripotent cells in a contacted cell population, quantitative real-time polymerase chain reaction (qRT-PCR) (e.g., monitor the absence or reduction in the gene expression of pluripotency markers), or flow cytometry (e.g., monitor the absence or reduction in the protein level of pluripotency markers). As used herein, the term "substantially differentiated" cell population refers to a population of cells containing at least about 50%, preferably at least about 60%, 70%, or 80%, and even more preferably, at least about 90%, differentiated cells representing one or more stem cell-derived cell types.

In general, methods of the invention are effected by contacting a cell, cell population, or sample with a chemical or compound according to the invention. More particularly, methods of the present invention can include contacting an effective amount of a chemical or compound to a heterogeneous cell population that comprises undifferentiated pluripotent stem cells and differentiated cell types derived from pluripotent stem cells, whereby the contacting selectively reduces or eliminates undifferentiated pluripotent stem cells from the cell population or sample. Chemicals and compounds appropriate for use according to a method provided herein exhibit selectivity in inhibiting or eliminating pluripotent stem cells without damaging other (e.g., differentiated) cell types. A chemical or compound that "selectively" inhibits or eliminates an undifferentiated pluripotent stem cell is a chemical or compound that inhibits the viability or promotes the death of an undifferentiated pluripotent stem cell, but does not substantially inhibit the viability or promote the death of a differentiated cell type. As used herein, the term "inhibits," "inhibition," or "inhibiting" refer to a decrease by any value between 10% and 90%, or of any integer value between 30% and 60%, or over 100%, or a decrease by 1-fold, 2-fold, 5-fold, 10-fold, or more. As used herein, the terms "promote" or "promoting" refer to an increase by any value between 10% and 90%, or of any integer value between 30% and 60%, or over 100%, or an increase by 1-fold, 2-fold, 5-fold, 10-fold, or more.

Any appropriate chemical or compound can be used according to the presently described methods. In some embodiments, a chemical or compound appropriate for use according to a method provided herein is capable of suppressing the activity or expression of $NAD^+$ (nicotinamide adenine dinucleotide), a coenzyme that plays a critical role in many physiologically essential processes (Ziegkel, *Eur. J. Biochem.* 267:1550-1564 (2000)). $NAD^+$ synthesis is mediated by NAMPT (nicotinamide phosphoribosyltransferase), an enzyme that converts nicotinamide to nicotinamide mononucleotide, which is converted into nicotinamide adenine dinucleotide (NAD+) by nicotinamide mononucleotide adenylyltransferase in the mammalian biosynthetic pathway. Since NAMPT is the rate-limiting factor in $NAD^+$ biosynthesis, NAMPT inhibitors deplete intracellular $NAD^+$ levels. Small-molecule NAMPT inhibitors include, without limitation, STF-31 (Chan et al., *Sci Transl Med.* 3:94ra70

(2011)); FK866 (also known as APO866); GNE-617 (N-{[4-(3 5-difluorobenzenesulfonyl)phenyl]methyl} imidazo[1,2-a]pyridine-6-carboxamide); GNE-618(N-(4-((3-(trifluoromethyl)phenyl)-sulfonyl)benzyl)-1H-pyrazolo [3,4-b]pyridine-5-carboxamide); and GMX-1778 (also known as CHS828).

FK866 has been shown to selectively block proliferation and induce apoptosis of activated T cells (Busso et al., *Plos One* 3:e2267 (2008)). STF-31 (also known as 4-[[[[4-(1,1-Dimethylethyl)phenyl]sulfonyl]amino]methyl]-N-3-pyridinyl-benzamide) has the empirical formula $C_{23}H_{25}N_3O_3S$, is soluble in DMSO, and is commercially available from distributors such as Tocris, EMD Millipore (Merck KGaA). GNE-617 was previously described by Zheng et al., *J Med Chem.* 56:6413-6433 (2013). GNE-618, which is structurally related to GNE-617, was previously described by Zheng et al., *Bioorg Med Chem Lett.* 23:5488-5497 (2013). GMX-1778 has been described as a potent and specific inhibitor of the $NAD^+$ biosynthesis enzyme NAMPT (Watson et al., *Molecular and Cellular Biol.* 29(21): 5872-5888 (2009)). See also von Heideman et al., *Cancer Chemother. Pharmacol.* 65(6):1165-72 (2010). Other NAMPT inhibitors appropriate for the methods provided herein include, without limitation, those compounds having structural similarity to STF-31 (see International Application No. PCT/US2012/022113) or GNE-617/618 as described in Dragovich et al., *Bioorg Med Chem Lett.* 24(3):954-62 (2014); Zheng et al., *J Med Chem,* 56(16):6413-33 (2013); and Zheng et al., *Bioorg Med Chem Lett,* 23(20):5488-97 (2013). For example, compounds having structural similarity to STF-31 for use according to a method provided herein include, without limitation, 4-(Phenylsulfonamidomethyl)-N-(quinolin-5-yl)benzamide (Vitas, STK647082); 4-tert-Butyl-N-(4-(pyridin-3-ylcarbamoyl)benzyl)benzamide (Otava Chemicals, 6360023); and 4-((4-Methoxyphenylsulfonamido)methyl)-N-(pyridin-3-yl)benzamide (Vitas, STK643640).

An effective amount of a chemical or compound for use according to a method provided herein can be a concentration between about 1 nanomolar (nM) to about 100 micromolar (µM) (e.g., about 0.5 nM, 1 nM, 5 nM, 10 nM, 15 nM, 20 nM, 25 nM, 30 nM, 50 nM, 75 nM, 90 nM, 0.1 µM, 0.5 µM, 1 µM, 1.5 µM, 2 µM, 2.5 µM, 3 µM, 3.5 µM, 4 µM, 4.5 µM, 5 µM, 10 µM, 15 µM, 20 µM, 30 µM, 40 µM, 50 µM, 60 µM, 70 µM, 80 µM, 90 µM, 100 µM). In some cases, an effective amount of a chemical or compound for use according to a method of the invention is a concentration of about 1 µM to about 2.5 µM (e.g., about 1, about 1.5, about 2, about 2.5 µM). As used herein, an effective amount is an amount of a chemical or compound capable of eliminating pluripotent stem cells (e.g., hPSCs). The half-maximal effective concentration can be presented as an $EC_{50}$ value. An effective amount of STF-31 is about 2.5 µM, which is substantially less than effective amounts of either benzethonium chloride or methylbenzethonium chloride (e.g., greater than 5 µM compared to 1 µM STF-31). An effective amount of FK866 is about 1.0 nM to about 25 nM (e.g., about 0.5 nM, 1 nM, 5 nM, 10 nM, 15 nM, 20 nM, 25 nM). Selective inhibition of pluripotent stem cells has been described following exposure to 20 µM PluriSin #1 (Ben-David et al., *Cell Stem Cell* 12(2):167-179 (2013)).

Chemicals and compounds appropriate for use according to a method provided herein can be contacted to a cell, cell population, or sample for any appropriate length of time. For example, an effective amount of a chemical or compound capable of eliminating pluripotent stem cells can be contacted to a heterogeneous cell population for a time sufficient to ensure elimination of all pluripotent stem cells from the cells, cell population, or sample. In some cases, a sufficient length or period of time is at least 1 hour, 2 hours, 6 hours, 12 hours, 24 hours, 48 hours, 60 hours, 72 hours, or 96 hours. For example, cells can be exposed to a chemical or compound such as STF-31 or FK866 for about 72 hours plus supplementation with compound in fresh culture medium every 24 hours. There can be an inverse relationship between the effective amount of chemical or compound used and the length of time required to selectively eliminate pluripotent stem cells. In other words, the length of exposure can decrease as the effective amount of, for example, the compound (e.g., STF-31, FK866) increases.

The effectiveness of a chemical or compound in eliminating undifferentiated pluripotent stem cells from a cell population can be confirmed (qualitatively or quantitatively) by detecting the presence or absence of undifferentiated pluripotent stem cells, assessing expression of differentiated cell type-specific markers, or determining cell viability following contacting or exposure to a chemical or compound that selectively inhibits or eliminates undifferentiated pluripotent stem cells. RNA or proteins can be extracted from the cells and assayed (via Northern hybridization, RT-PCR, Western blot analysis, etc.) for the presence of markers indicative of a desired phenotype. For example, pluripotent stem cells can detected by various cell surface markers, including SSEA-3, Tra-1-60, and Tra-1-81. $SSEA-3^+$ cells can be detected using a chromophore-conjugated antibody having specificity to that particular antigen. In some cases, one or more cell surface markers correlated with an undifferentiated state (e.g., SSEA-4, Tra-1-60, and Tra-1-81), as well as the pluripotent stem cell transcription factor marker, Oct-4, can be detected. Also, undifferentiated pluripotent stem cells have typical stem cell morphology, which is well described in the art.

Differentiated cell types such as cardiomyocytes can be identified using qRT-PCR to detect expression of cardiac markers such as NKX2.5 or TNNT2. Adult multipotent stem cells can be identified based upon high expression levels of the enzyme aldehyde dehydrogenase (ALDH). Of course, cells can be assayed immunohistochemically or stained, using tissue-specific stains. In other cases, telomere length can be used as an indicator of differentiation. In general, undifferentiated stem cells have longer telomeres than differentiated cells; thus the cells can be assayed for the level of telomerase activity.

Cell viability can be assessed by measuring a percentage of viable cells following one or more exposures to a compound such as STF-31. Cell viability can be demonstrated by various methods including, without limitation, exclusion of a vital dye such as trypan blue or 7-amino-actinomycin D (7-AAD), loss of uptake of neutral red (3-Amino-7-dimethylamino-2-methylphenazine hydrochloride), or reduction of the tetrazolium dye MTT 3-(4,5-dimethylthiazol-2-yl)-2,5-diphenyltetrazolium bromide to insoluble formazan.

In some cases, a cell population obtainable by a method provided herein is a stem cell-derived cell population devoid of, or substantially devoid of, undifferentiated pluripotent stem cells. Pluripotent stem cells include induced pluripotent stem (iPS) cells and embryonic stem (ES) cells, both of which are valuable sources of differentiated somatic cell types for research and clinical applications. Cells of a population obtainable by a method provided herein, therefore, can be multipotent, oligopotent, unipotent, or terminally differentiated cell types. As used herein, "multipotent cells" include cells and their progeny, which may be able to differentiate into, or give rise to, multipotent, oligopotent and unipotent progenitor cells, and/or one or more mature or partially mature cell types, except that the mature or partially mature cell types derived from multipotent cells are limited to cells of a particular tissue, organ or organ system. Multipotent stem cells include, without limitation, hematopoietic stem cells, neuronal stem cells, and bone marrow stem cells. Oligopotent stem cells include, without limitation, intestinal stem cells, mammary stem cells, myeloid or lymphoid precursor cells, cells from amniotic fluid, mesenchymal progenitor cells/multipotent stromal cells/mesenchymal stem cells (MSCs), glial-restricted precursor cells, bipotential precursor cells from fetal liver, peripheral blood mononuclear cells, mast cell precursor cells, satellite cells, dermal stem cells, hair follicular stem cells, basal stem cells, hematopoietic cells, myeloid precursor cells, mesenchymal progenitor cells, glial-restricted precursor cells, bipotential precursor cells from fetal liver, umbilical cord blood cells, peripheral blood stem cells, cells from amniotic fluid, bone marrow stem cells, and mast cell precursor cells.

In some cases, a cell population obtainable by a method provided herein is substantially homogeneous, consisting essentially of a single stem cell-derived cell type (e.g., cardiomyocytes, neurons, liver cells, neural stem cells, hematopoetic stem cells). Any appropriate method can be performed to detect the presence of undifferentiated pluripotent stem cells in a cell population obtained according to a method provided herein. For example, assays can be performed to assess the potential for a cell population or subset thereof to form tumors comprising cells derived from all three germ layers such as teratomas, teratocarcinomas, or other germ cell tumors. In some cases, a teratoma assay includes injecting 1e3-5e6 human cells into a tissue or organ of an animal. kidney, testis, intramuscular, or subcutaneous. According to some teratoma assay protocols, tumors resulting from the injection are assessed by certified pathologist 6-12 weeks after transplantation or once tumor diameter reaches defined endpoint. For review, see Wesselschmidt, R. L., *Methods Mol Biol.* 767:231-41 (2011); Zhang et al., *Teratoma formation: A tool for monitoring pluripotency in stem cell research*, in *Stem Book* 2008: Cambridge (Mass.).

Differentiated cell types appropriate for cell populations of the present invention include any differentiated cell type of the three germ layers, endoderm, mesoderm, and ectoderm. In some cases, differentiated cells include, without limitation, stem cell-derived cardiomyocytes, neural progenitors, neurons, vascular smooth muscle cells (obtained from multiple lineages), endothelial cells, neurons, retinal pigmented epithelial cells, liver cells, and mesenchymal stem cells.

In another aspect, the present invention provides an isolated population of stem cell-derived cells obtained by a method described herein. Populations of stem cell-derived cell types that are free or substantially free of undifferentiated pluripotent stem cells are useful for research and clinical applications, including tissue engineering.

In a further aspect, the present invention provides therapeutic formulations comprising one or more compounds that selectively reduce or eliminate undifferentiated pluripotent stem cells from a cell population. Preferably, a therapeutic formulation provided herein will be formulated, dosed, and administered in a fashion consistent with good medical practice. Factors for consideration in this context include the particular disorder being treated, the particular mammal (e.g., human) being treated, the clinical condition of the individual patient, the cause of the disorder, the site of delivery of the agent, the method of administration, the scheduling of administration, and other factors known to medical practitioners. The compound (e.g., NAMPT inhibitor) need not be, but is optionally formulated with one or more agents currently used to prevent or treat cancer or to treat or prevent another clinical disease or disorder. Preferably, a therapeutic formulation provided herein is prepared by mixing one or more compounds that selectively reduce or eliminate undifferentiated pluripotent stem cells from a cell population with a physiologically acceptable carrier, excipient, or stabilizer. In exemplary embodiments, the therapeutic formulation is prepared in the form of a lyophilized formulation or aqueous solution.

Also provided herein are methods comprising administration of therapeutically effective amount of a compound or therapeutic formulation thereof to a subject in need thereof. As used herein, a "therapeutically effective amount" of the compound or therapeutic formulation to be administered will be an amount necessary to deplete substantially all pluripotent cells from a complex mixture; or to decrease the number of teratoma cells in a subject. In exemplary embodiments, chemicals, compounds, and formulations of the present invention are useful in vitro and in vivo for depletion of pluripotent stem cells, including the prevention of teratoma formation upon administration of a stem cell-derived cell population provided herein.

Acceptable carriers, excipients, or stabilizers are non-toxic to recipients at the dosages and concentrations employed, and include buffers such as phosphate, citrate, and other organic acids; antioxidants including ascorbic acid and methionine; preservatives (such as octadecyidimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Formulations to be used for in vivo administration must be sterile. This is readily accomplished by filtration through sterile filtration membranes.

The therapeutic dose may be at least about 0.01 µg/kg body weight, at least about 0.05 g/kg body weight; at least about 0.1 g/kg body weight, at least about 0.5 g/kg body weight, at least about 1 µg/kg body weight, at least about 2.5 g/kg body weight, at least about 5 µg kg body weight, and not more than about 100 µg/kg body weight. It will be understood by one of skill in the art that such guidelines will be adjusted for the molecular weight of the active agent. The dosage may also be varied for localized administration, e.g., for systemic administration, e.g., i.m., i.p., i.v., and the like.

In another aspect, provided herein is a method of suppressing tumorigenicity of cells administered to a subject. As used herein, the terms "tumorigenicity" and "tumorigenic property" refer to the ability, tendency, or capability to cause, produce or develop tumors. The tumor may be benign (not cancerous), potentially malignant, pre-malignant (pre-cancerous), or malignant (cancerous). Examples of the benign, potentially malignant, or pre-malignant tumor used herein include, without limitation, adenoma, polyp, and teratoma. Suppressing or reducing tumorigenicity includes reducing or preventing one or more tumorigenic properties of cells. Preferably, a method of suppressing tumorigenicity comprises administering to the subject in need thereof a cell composition comprising pluripotent stem cell-derived cells that have been contacted to an effective amount of a compound that selectively reduces or eliminates undifferentiated pluripotent stem cells or partially differentiated pluripotent stem cell derived progeny (e.g., a NAMPT inhibitor). Contacting to the compound can occur prior to, at the time of, or subsequent to administration of the cell composition to the subject to suppress tumorigenicity (e.g., potential for teratoma formation) of the administered cell composition. For contacting cells to the compound at the time of administration or subsequent to administration of the cell composition to the subject, an effective amount of the compound can be between about 0.1 to 0.126 mg/m$^2$/hour. Preferably, the subject is a human. Cells of the cell composition can be allogeneic or autogeneic to the subject. Preferably, suppressing or reducing tumorigenicity includes reducing, attenuating, or preventing one or more tumorigenic or potentially tumorigenic properties of any cells within the cell composition. For example, a method of the present invention is effective for inhibiting, suppressing, or reducing a tumorigenic property of a cell composition if upon treatment of the cell population according to a method provided herein, the cell composition exhibits properties more similar to those properties of (or those not found in) a cell composition comprising non-tumorigenic cells of the same species.

In a further aspect, the present invention provides methods for obtaining a cell composition having reduced tumorigenicity for transplantation into a subject. In exemplary embodiments, the method comprises providing a population of pluripotent stem cell-derived cells; and contacting the population to an effective amount of a compound that selectively reduces or eliminates undifferentiated pluripotent stem cells or partially differentiated pluripotent stem cell derived progeny (e.g., a NAMPT inhibitor), whereby the contacted population has reduced tumorigenicity relative to a pluripotent stem cell-derived cell population not contacted to the compound, and using the contacted population as a cell population for transplantation into the subject. Preferably, the subject is a human. Cells of the cell composition can be allogeneic or autogeneic to the subject.

Articles of Manufacture

In another embodiment of the invention, provided herein is an article of manufacture containing materials useful for methods of selectively reducing or eliminating undifferentiated pluripotent stem cells in vitro or in vivo. The article of manufacture comprises a container and a label. Suitable containers include, for example, bottles, vials, syringes, and test tubes. The containers may be formed from a variety of materials such as glass or plastic. In some cases, the container holds a therapeutic formulation provided herein and may have a sterile access port (for example the container may be an intravenous solution bag or a vial having a stopper pierceable by a hypodermic injection needle). The active agent in the composition is a chemical or compound that selectively reduces or eliminates undifferentiated pluripotent stem cells, or cocktail of two or more of such compounds. The label on, or associated with, the container indicates that the composition is used for the in vitro and in vivo applications described herein. The article of manufacture may further comprise a second container comprising a pharmaceutically-acceptable buffer, such as phosphate-buffered saline, Ringer's solution, and dextrose solution. It may further include other materials desirable from a commercial and user standpoint, including other buffers, diluents, filters, needles, syringes, and package inserts with instructions for use.

While the present invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents and alternatives falling within the spirit and scope of the invention as defined by the appended claims.

The invention will be more fully understood upon consideration of the following non-limiting Examples.

EXAMPLES

Example 1—Inhibition of an NAD$^+$ Salvage Pathway Provides Efficient and Selective Toxicity to Human Pluripotent Stem Cells Human embryonic stem cells (hESC) and induced pluripotent stem cells (hiPSC), collectively termed human pluripotent stem cells (hPSC), can differentiate into almost any human cell type. Although significant progress has been made in developing effective strategies for the differentiation of hPSC to progeny useful for drug toxicity testing and human disease modeling [1-4], continued safety issues preclude their broad use for human therapeutics. Cell heterogeneity, purity, and mode of transplantation are technically problematic, but the potential formation of teratomas at the site of transplantation represents a significant obstacle for clinical applications. Teratoma formation has been reported in animal models following transplantation of low numbers of mouse and human PSC [5, 6] and after injection of hPSC-derived cells [7-10]. Pre-clinical testing of hESC-derived neural progenitor cells in the Geron trial also resulted in cyst formation in the spines of mice, suggesting additional limitations for transplantation of hESC products in human subjects [11]. Therefore, the elimination of potentially tumorigenic pluripotent stem cells prior to transplantation is required before hPSC-based therapies can become widely available.

Figure 9:
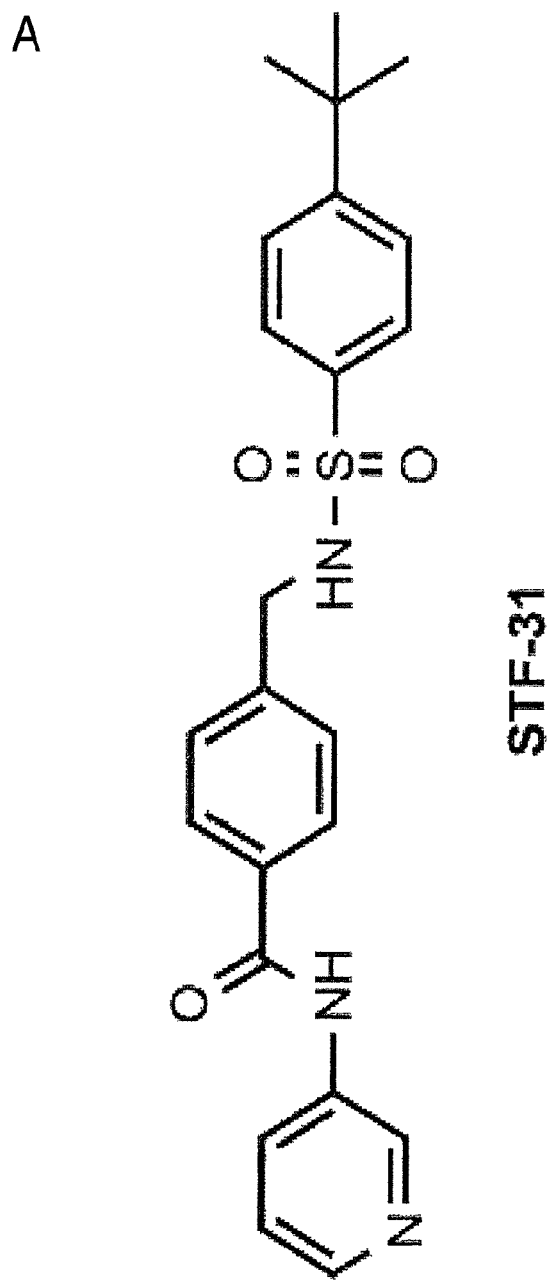
FIG. 9 presents the chemical structures of (A) STF-31 and (B) FK866, a non-competitive inhibitor of NAMPT.
Figure 9:
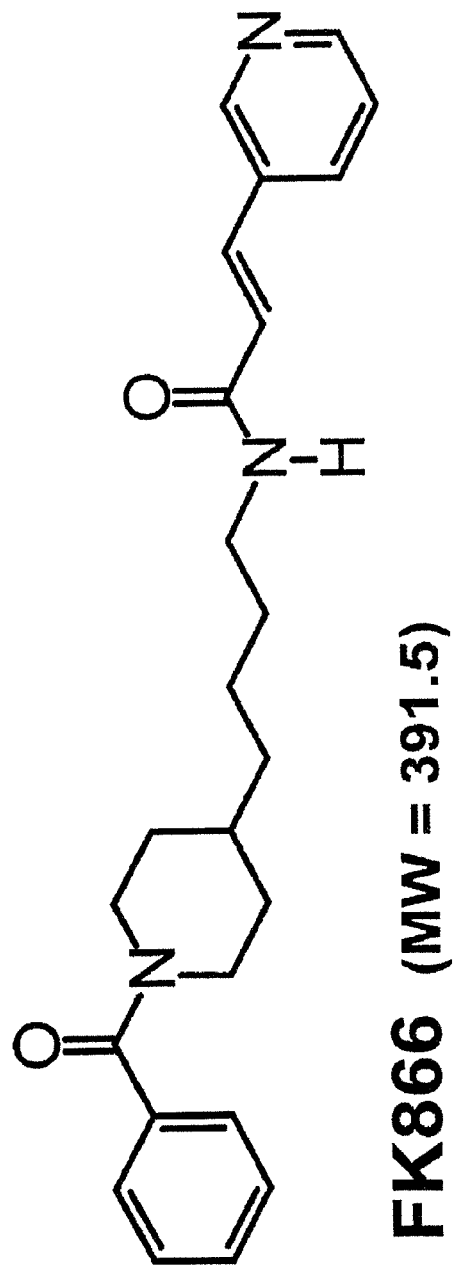

Here, we present data demonstrating that STF-31 (chemical structure shown in FIG. 9A) effectively eliminates these potentially tumorigenic cells across a range of culture conditions by a process that spares differentiated progeny. These results provide an important advancement towards the development of clinically safe hPSC-derived progeny for human stem cell based therapies.

Figure 5:
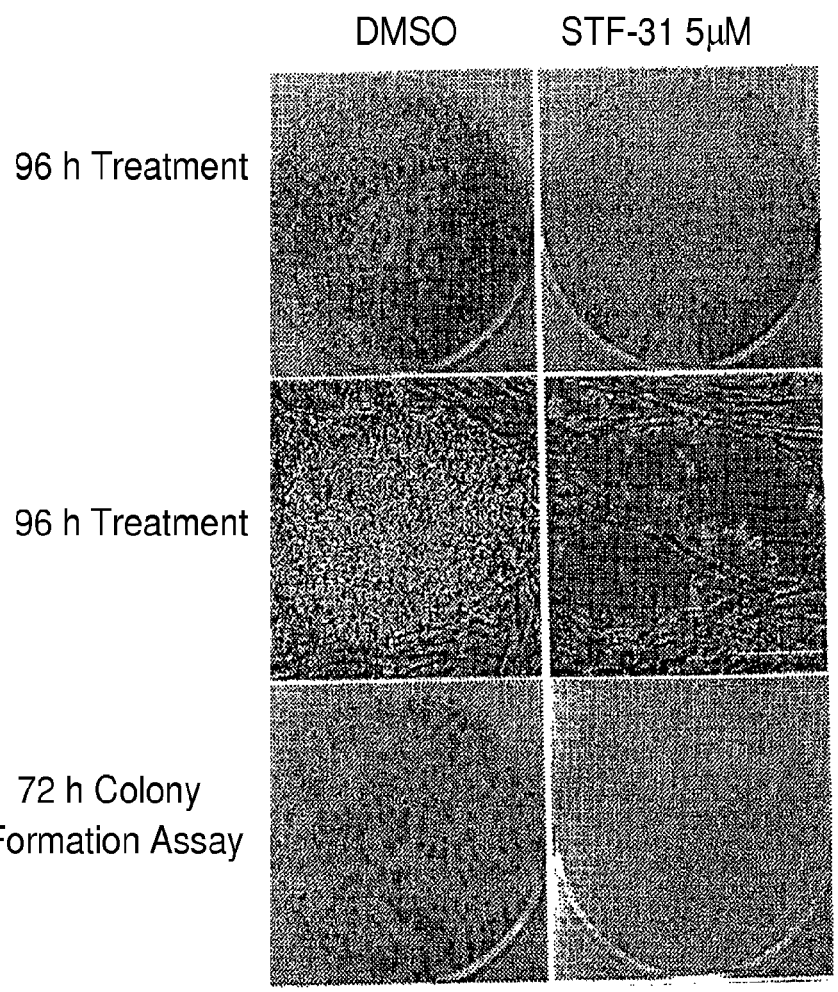
FIG. 5 presents data demonstrating that STF-31 is toxic to human embryonic stem cells (hESCs) when cultured in the presence of fibroblasts. (A) Representative images of alkaline phosphatase staining (top panel) and brightfield imaging (middle panel) of H1 hESC colonies grown on mitotically inactivated human fibroblast feeders after 96 hours of continuous treatment with 2.5 µM STF-31. Representative images of staining for alkaline phosphatase activity in H1 colonies. 72 hours after passaging colonies treated with vehicle control or STF-31 for 96 hours with 2.5 µM STF-31 (N=3). (B) Representative density plots of co-staining for BrDU incorporation and 7-AAD in discontinuously proliferating hiPSC 24-96 hours post-plating. * $p \leq 0.05$, *** $p \leq 0.001$ compared to DMSO control. (C) Representative images of alkaline phosphatase staining to detect DF6-9-9T hiPSC colonies in co-cultures with day 10 cardiomyocytes. DF6-9-9T were plated between 1e2 and 1e4 live cells and treated for 24 hours with 5 µM STF-31 24 hours after plating (N=2).
Figure 5:
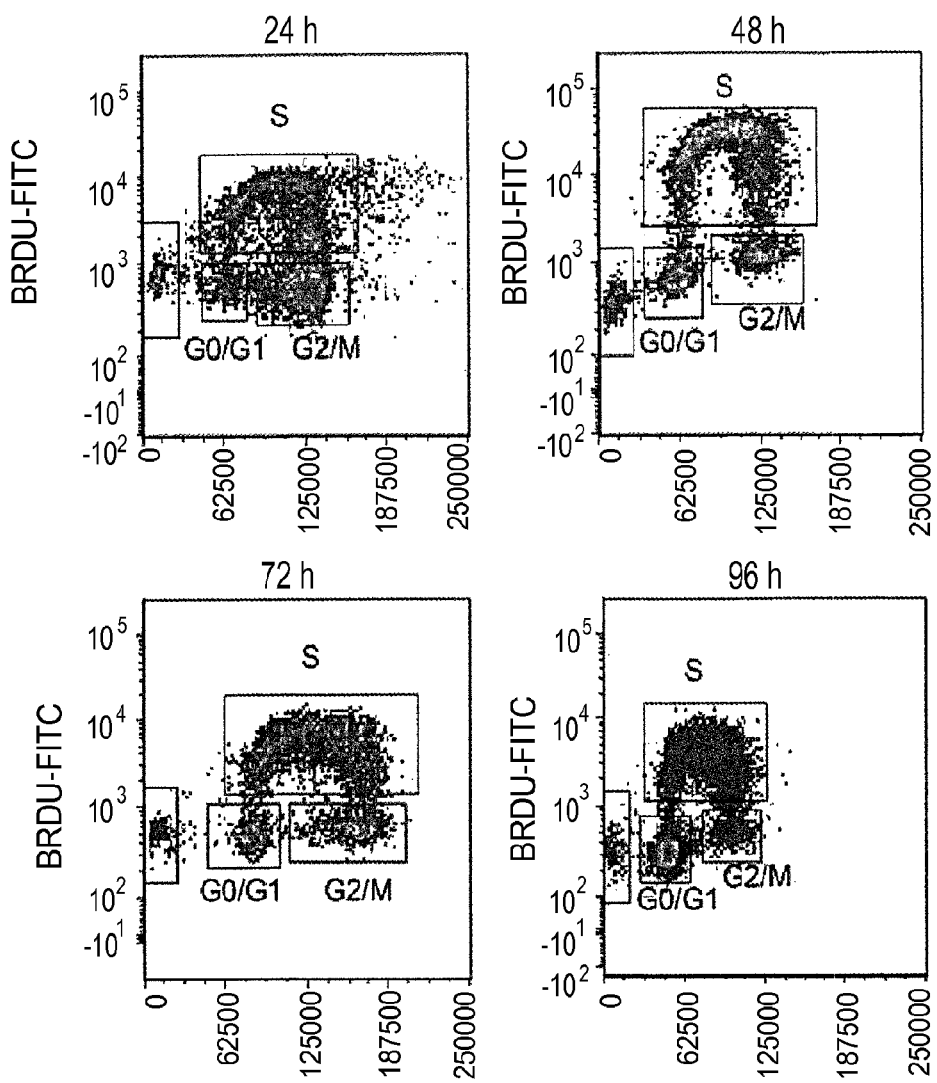
Figure 5:
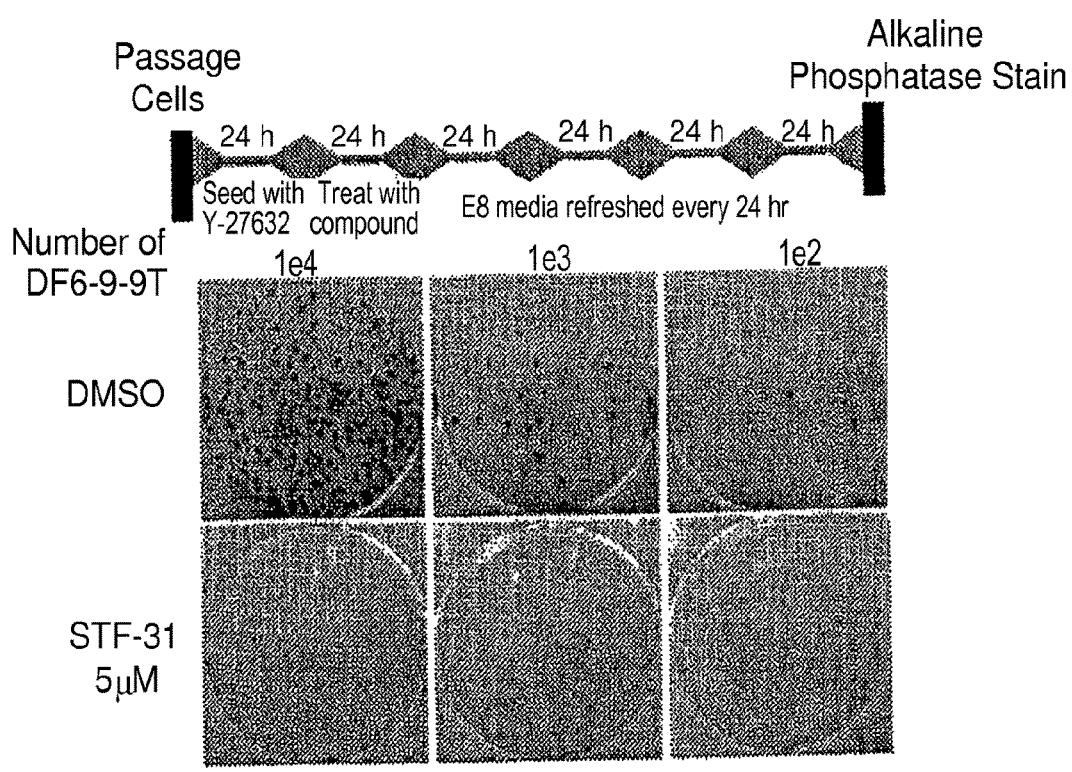

STF-31 and WZB117 mediated toxicity in hPSC were directly compared to PluriSIn, a previously reported small molecule used for hPSC elimination. Treatment with STF-31 did not modify the morphology of hiPSC following a 24 hour incubation (FIG. 1A). However, patches of diminished, non-adherent cells and reduction in overall cell number were observed following 48 hour treatment (FIG. 1A). After 72 hours of exposure, STF-31 was highly toxic with a limited number of cells remaining. In contrast to STF-31, it took 72 hours of treatment with WZB117 to cause morphological changes such as cell swelling, while there were minimal alterations in the morphology of PluriSIn treated cells. These morphological changes are consistent with biochemical assays of cell viability. STF-31 reduced cell viability to 10% following 72 hours treatment as determined by the SYTOX® Green nucleic acid stain (FIG. 1B). In contrast, there was no significant reduction in the viability of PluriSIn or WZB117 treated cells. As the SYTOX® assay relies on the presence of dead cells to quantify viability; we also performed live/dead staining by calcein AM and ethidium homodimer-1 (FIG. 1C). Following 48 hours of STF-31 treatment, small patches of live cells remained. These live cells were not visible by 72 hours of treatment. In contrast, WZB117 and PluriSIn were not toxic to confluent hPSC. Because STF-31 appeared to be the most robust small molecule for the elimination of hPSC cultured under these conditions, we determined the median lethal dose ($LD_{50}$) of STF-31 for hiPSC to be 182 nM STF-31 48 hours after continuous treatment (FIG. 1D). Increasing STF-31 concentrations to 100 µM did not accelerate the time at which significant toxicity was observed by neutral red assay (FIG. 1D; FIG. 5A).

Figure 6:
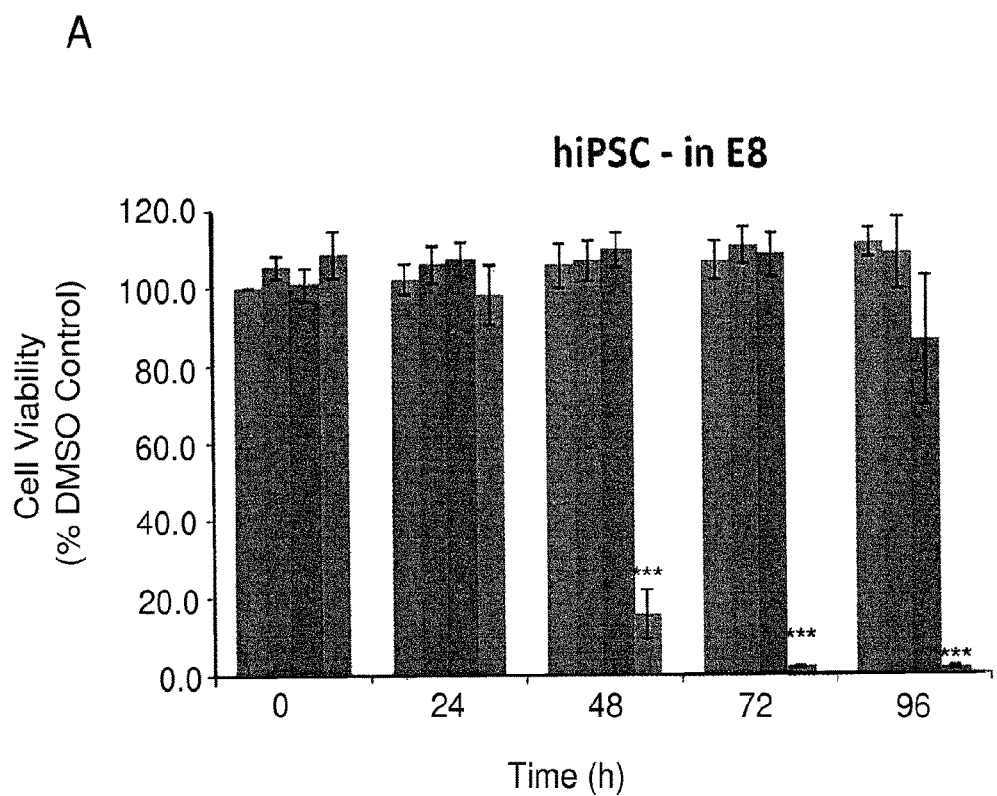
FIG. 6 demonstrates the effects of media, timing, and concentration on PluriSIn- and STF-31-mediated toxicity. (A-B) Bar graphs representing cell viability in E8 media after 24-96 h treatment with 20-40 µM PluriSIn and 2.5 µM STF-31 as measured by neutral red assay in confluent hiPSC (DF6-9-9T; a) and hESC (H1; b) (N=3). (C-D) Bar graphs representing cell viability in mTeSR media after 24-96 hours treatment with 20 µM PluriSIn and 2.5 µM STF-31 as measured by neutral red assay in confluent hiPSCs (c) and hESCs (d) in mTeSR media (N=3). * $p \leq 0.05$,  $p \leq 0.01$, * $p \leq 0.001$ compared to DMSO control.
Figure 6:
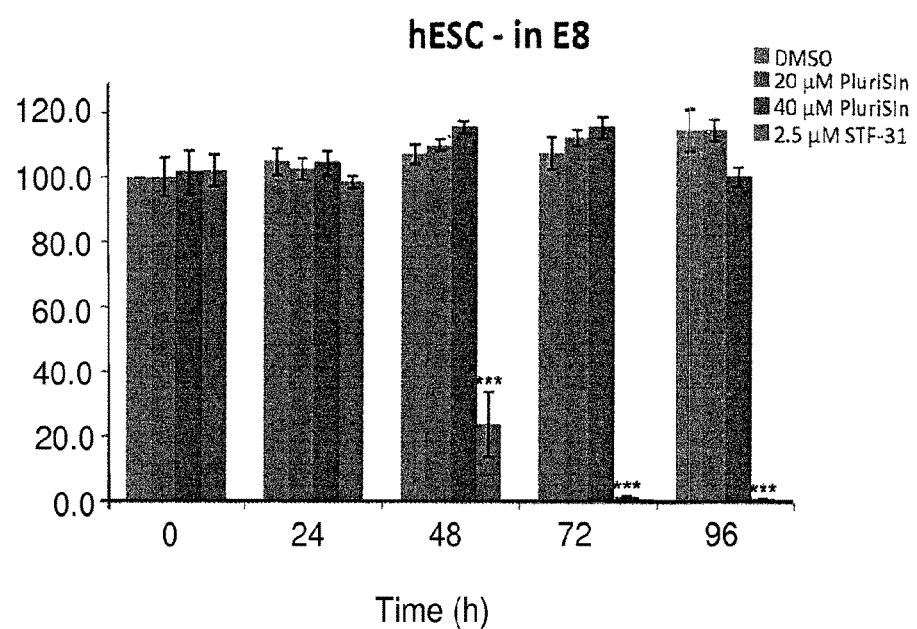
Figure 6:
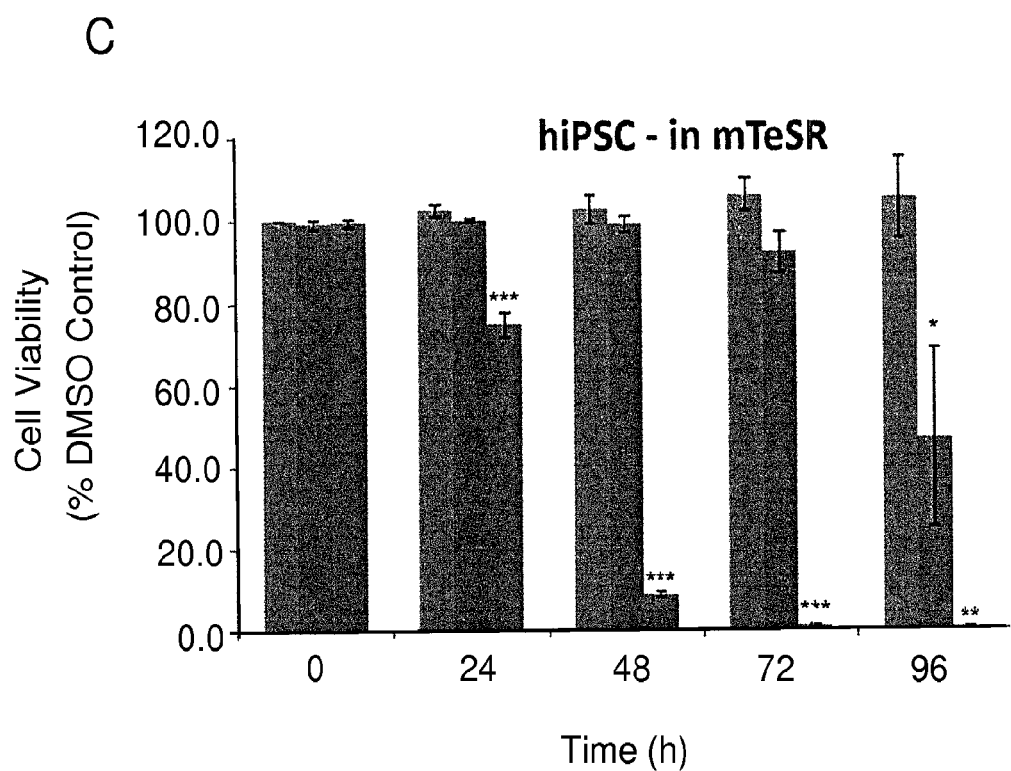
Figure 6:
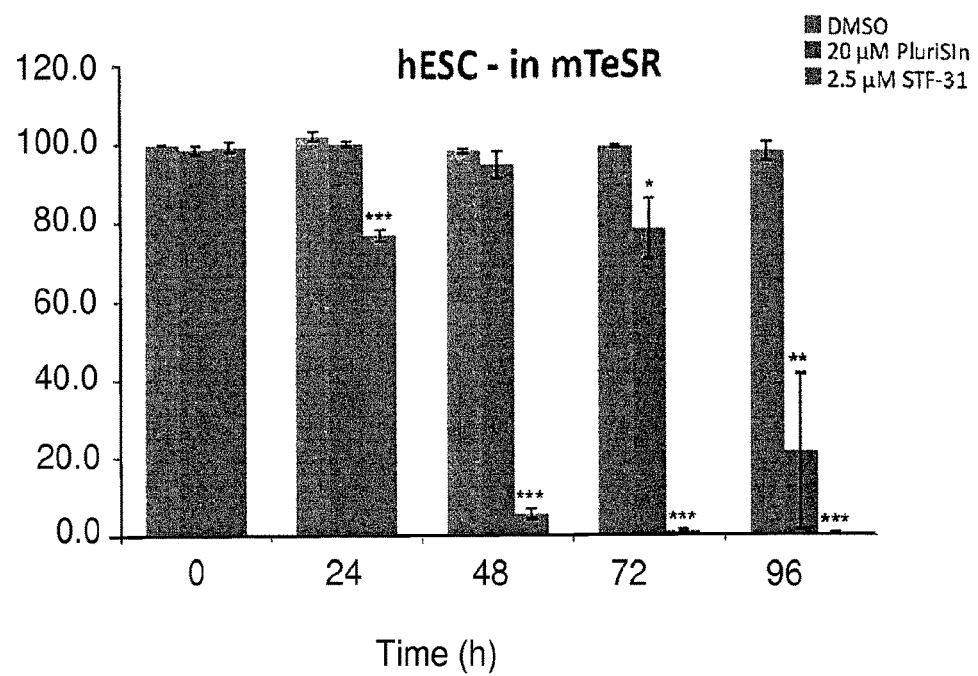

Because we were unable to fully reproduce the previously reported toxic effects of PluriSIn on human pluripotent stem cells, we tested alternative culture conditions. Sub-confluent and confluent cells were generated either by plating cells at the same density and allowing them to grow for different lengths of time (24 vs 96 hours), or by plating the cells at two different densities (1.5e5 vs 7.5e5 cells/$cm^2$) and allowing them to grow for 24 hours (FIG. 1E). For each cell density condition, cells were treated with STF-31, PluriSin, or WZB117 for 72 hours. In these comparisons, the time required to detect STF-31 mediated toxicity was similar for both confluent and sub-confluent cells; with fewer than 2% viable cells remaining 72 hours after start of treatment. In contrast, toxicity of WZB117 and PluriSIn varied among the conditions (FIG. 1E). WZB117 was toxic to sub-confluent cells and confluent cells that were treated 24 hours post-plating, but was significantly less toxic to confluent cells that were treated 96 hours post-plating. PluriSIn was only effective on sub-confluent cells and did not induce significant toxicity in confluent cells. Moreover, increasing concentrations of PlurSIn did not result in cell death in confluent cells (FIG. 6). Importantly, cell death in response to each of the compounds was similar among three hESC (H1, H7, H9) (data not shown) and two hiPSC (KB3, DF6-9-9T) lines (FIG. 1; some data not shown), as well as between hPSC cultured in either E8 or mTesR media compositions (FIG. 6). Additionally, STF-31 was toxic to hESC colonies grown on human fibroblast feeder cells with toxicity occurring between 48-72 hours. Following 96 hours of treatment, toxicity was evaluated with brightfield microscopy and staining for alkaline phosphatase activity. Colonies were not detected with alkaline phosphatase staining; positive staining consisting of only non-adherent cells and acellular debris (FIG. 5A, top panel). Brightfield microscopy confirmed an absence of colonies with non-adherent cells with diminished morphology (FIG. 5A, middle panel). To confirm elimination of hESC, colonies were passaged 96 hours after treatment initiation and cultured for an additional 72 hours. No colony growth or alkaline phosphatase activity was detected in passaged cells, indicating elimination of hESC (FIG. 5A, lower panel).

Cell density is an important variable for many in vitro differentiation protocols utilized to generate tissue-specific progeny from hPSC (e.g., neuronal cells, hepatocytes, cardiomyocytes [19, 22, 24, 34]). Additionally, cell proliferation rates can also vary among common hPSC culture conditions and hPSC lines. To verify that STF-31 is toxic at various cell proliferation rates, hiPSC were incubated with 5-bromo-2-deoxyuridine (BrdU) (10 µM) 24-96 hours post-plating and the cell cycle was examined (FIG. 1F; FIG. 5B). At 24 hours post-plating (low densities), 8% of cells are in G0/G1 phase, while at 96 hours post-plating (high densities) 47% of the cells were in G0/G1 phase. Therefore, while all methods of elimination tested here were toxic to rapidly proliferating hPSC, STF-31 was the only agent toxic to hPSC across a broad range of hPSC densities and rates of proliferation. Thus, STF-31 mediated toxicity may be advantageous in confluent culture systems where hPSC may have altered proliferation rates.

The effectiveness of STF-31 for the prevention of hPSC self-renewal and tumorigenicity was evaluated in vitro with a colony formation assays alongside WZB117 and PluriSIn treatment. We determined that 24 hours was the minimal treatment time with STF-31 to achieve completetoxicity of hPSC (data not shown). Using a 24 hour pulse treatment scheme, we found that STF-31 prevented the formation of alkaline phosphatase-positive colonies from confluent hiPSC, whereas PluriSIn and WZB117 did not prevent colony growth (FIG. 1G). As a more stringent examination of the effectiveness of STF-31 for the removal of hiPSC, a colony formation assay was performed without cell passaging to eliminate exaggerated cell death caused by stress during the dissociation and re-plating of cells (FIG. 1H). In this strategy, STF-31, WZB117, and PluriSIn were applied for 24 hours to confluent hiPSC then media was replaced daily for six days. Similar levels of alkaline phosphatase-positive cells were observed in the DMSO, WZB117, and PluriSIn-treated hiPSC. In contrast, a limited number of colonies formed in hiPSC treated with 2.5 µM STF-31 and no colonies were observed in the hiPSC treated with 5 µM STF-31. These findings demonstrate that for confluent hiPSC, 24 hours treatment with STF-31 prevents reformation of alkaline phosphatase-positive colonies, while PluriSIn and WZB117 are ineffective against a confluent monolayer of hPSC.

Figure 2:
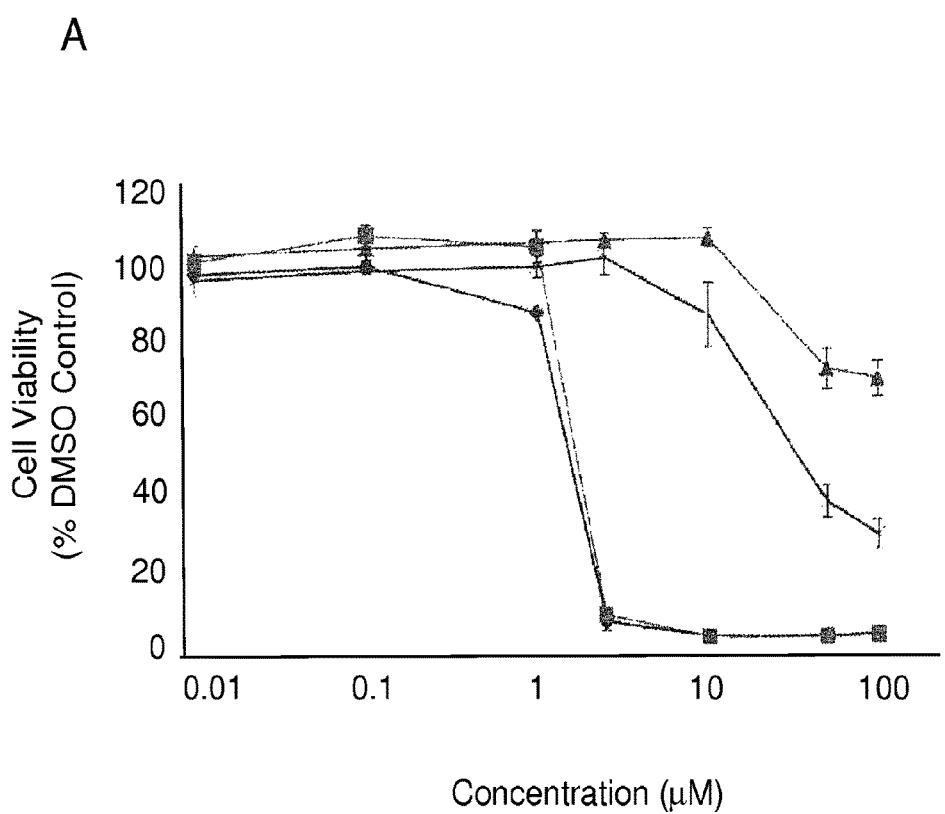
FIG. 2 presents data obtained for twenty-four hour pulse treatment for selective in vitro elimination of hiPSC. Titration (A) and comparison of small molecules (B) following 24 hours of treatment with STF-31 (0.01-100 µM), 30 µM WZB117, and 20 µM PluriSIn in sub-confluent and confluent hiPSC (DF6-9-9T), fibroblasts, and DF6-9-9T hiPSC-derived cardiomyocytes. Average viability was measured with neutral red assay 72 hours after treatment initiation (N=3). Representative flow cytometry histogram (C) of TNNI3 and IRX4 abundance in cardiomyoyctes 72 hours after initiation of a 24 hour treatment with 5 µM STF-31 (N=3). Representative images (D) for immunofluorescent detection of TNNT2 organization in day 15 cardiomyocytes following a 24-hour pulse treatment with 5 µM STF-31 on day 10 of differentiation. Top panel displays cell clusters imaged at 40× and the lower panel has individual cells showing structural organization imaged at 100× magnification. The scale bar in the top panel is 50 µm and the bottom panel is 20 µm (N=3). Bar graphs (E) for qPCR of TNNI3, TNNT2, and NKX2.5 24-72 hours after initiation of a pulse treatment with 5 µM STF-31 in day 10 cardiomyocytes. Representative images of alkaline phosphatase staining to detect DF6-9-9T hiPSC colonies in co-cultures with day 10 cardiomyocytes (F) and human fibroblasts (G). DF6-9-9T were plated between 1e2 and 1e4 live cells and treated for 48 hours with 5 µM STF-31 24 hours after plating (N=3 for cardiomyocytes and N=5 for human fibroblasts). Data are represented as mean±SEM. ** $p \leq 0.01$ compared to DMSO control.
Figure 2:
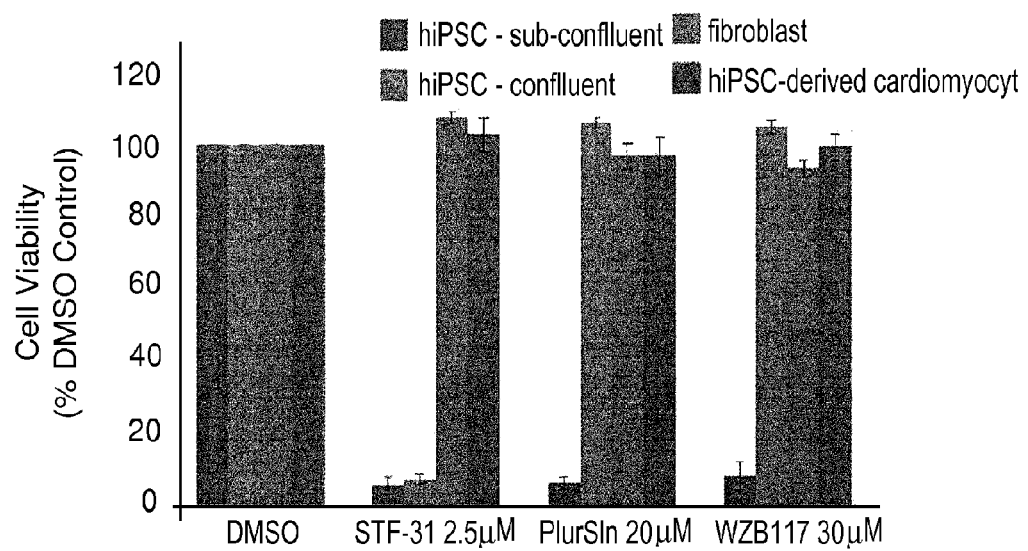
Figure 2:
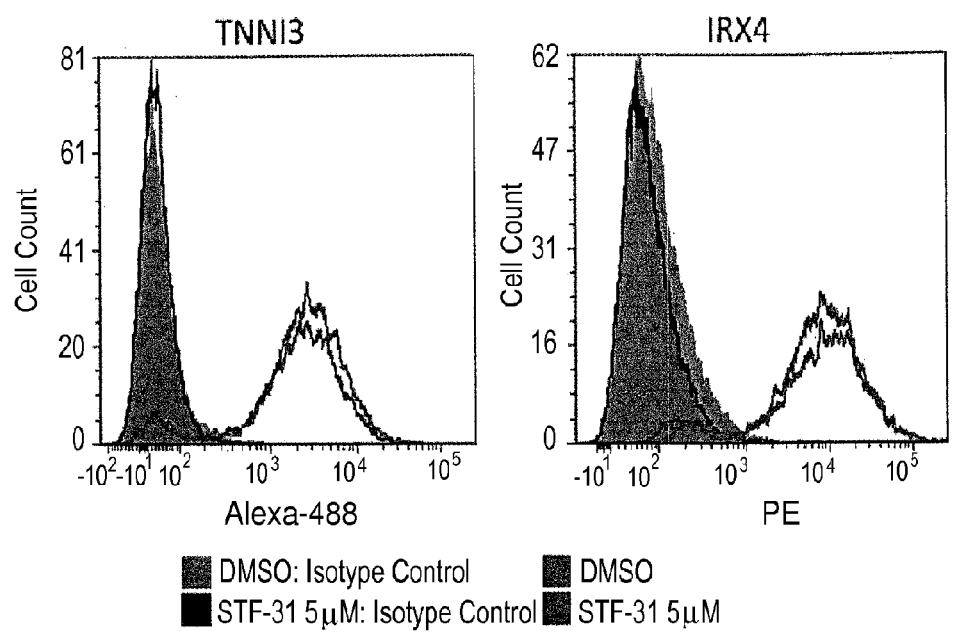
Figure 2:
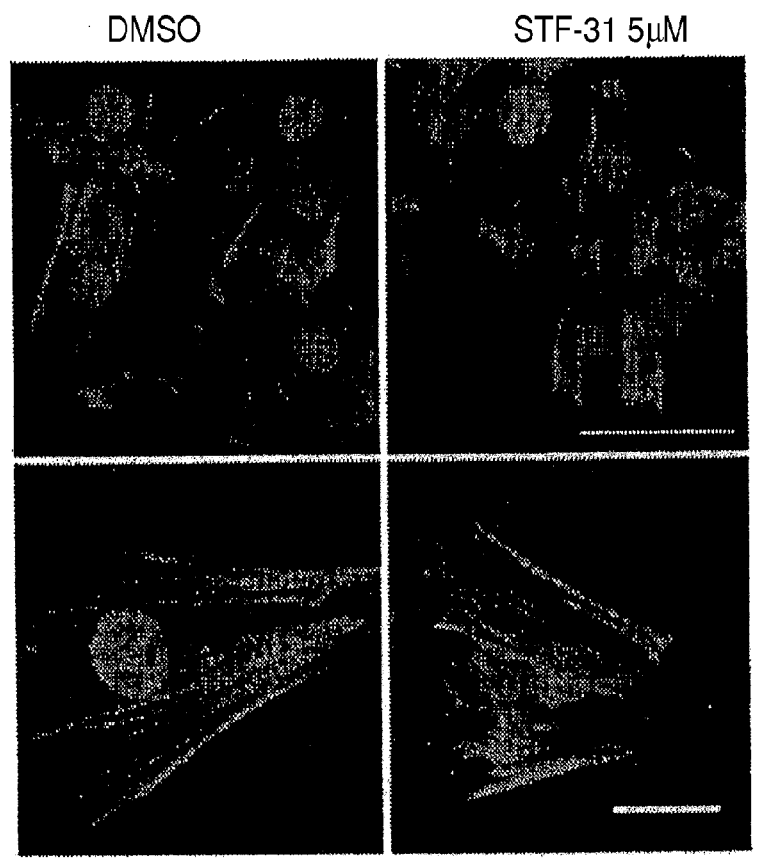
Figure 2:
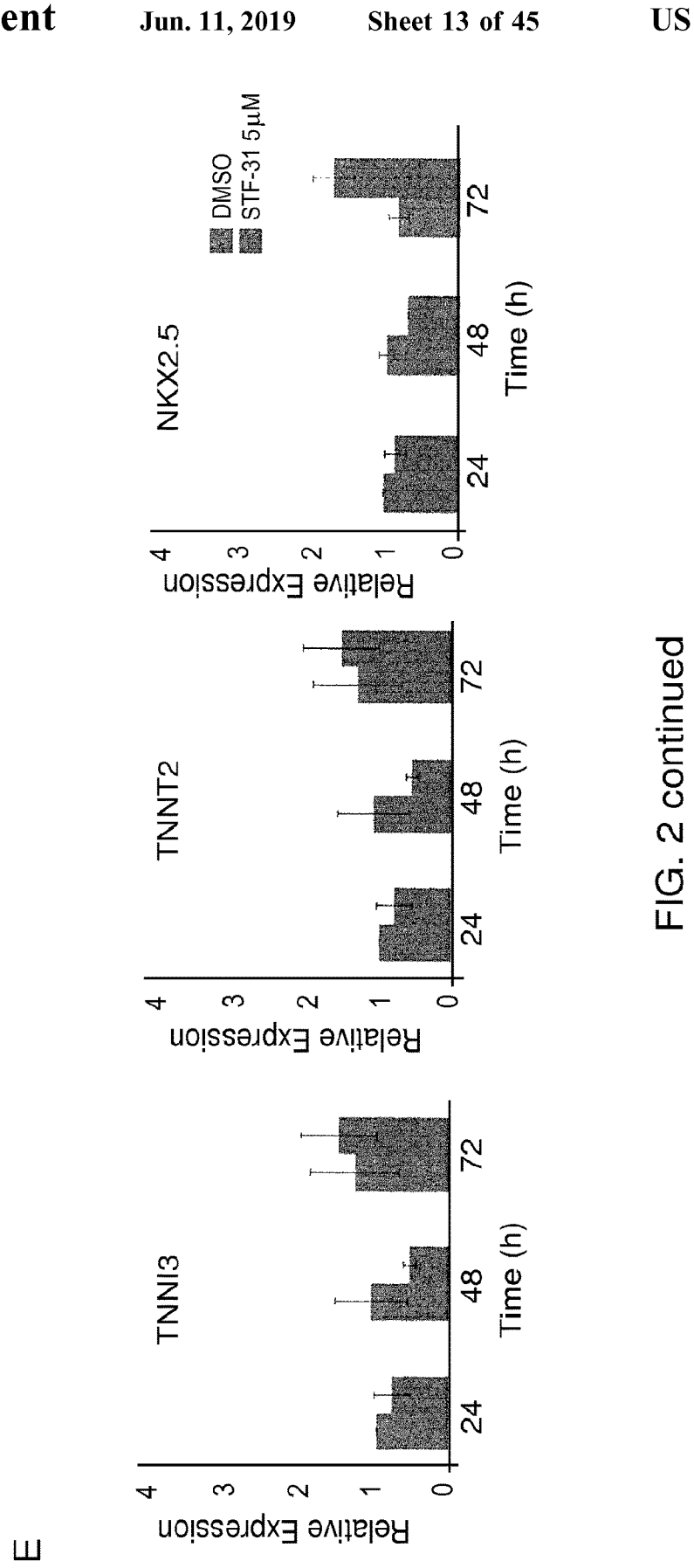
Figure 2:
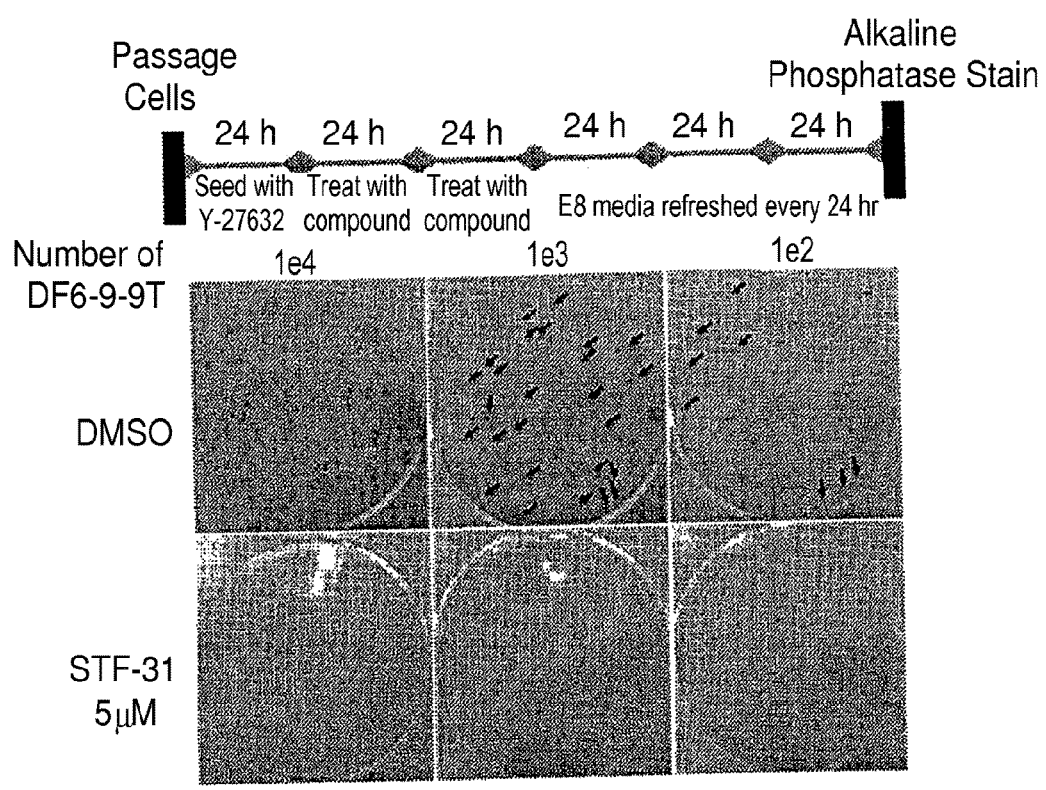
Figure 2:
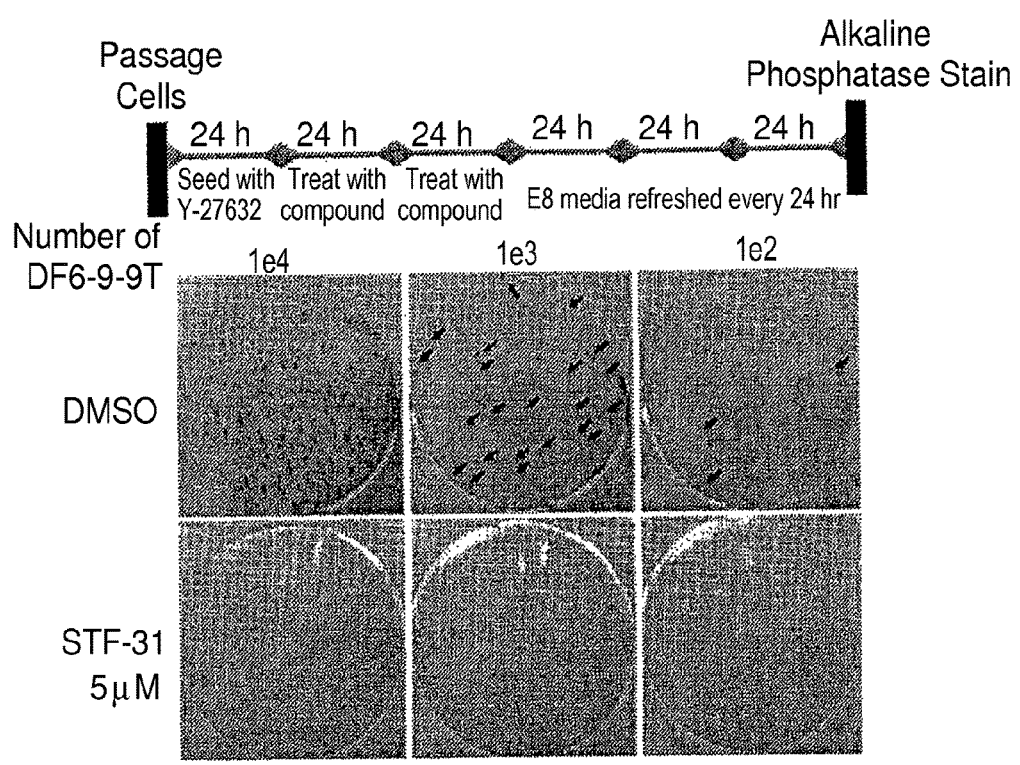

To further evaluate the utility of STF-31, we examined the effects of a 24 hour pulse treatment of STF-31 treatment on sub-confluent and confluent hiPSC as well as differentiated cells. The $LD_{50}$ of STF-31 was determined to be 1.35 µM and 1.78 µM when sub-confluent or confluent cells were treated, respectively (FIG. 2A). Consistent with the data in FIG. 1, 24 hour treatment with WZB117 and PluriSIn eliminated sub-confluent hiPSC, but not confluent hiPSC (FIG. 2B). 24 hour treatment with STF-31 did not appear to be toxic to human fibroblasts, as concentrations of 100 µM only reduced fibroblast viability by 30%. These data for the 24 hour treatment are consistent with our previous report that exposed fibroblasts to STF-31 for 72 hours continuously [19]. Using this 24 hour pulse treatment, the $LD_{50}$ of STF-31 on hiPSC-derived cardiomyocyte cultures was 40 µM, a 22-fold higher concentration than required for hiPSC (FIG. 2A). Extending the treatment time to 72 hours did not result in a decrease in cell viability with fully committed retinal pigmented epithelial cells (ARPE-19 line; data not shown) or fibroblasts [19].

Using the conditions established for hPSC elimination, (5 µM for 24 hours) the effects of STF-31 on day 10 cardiomyocyte function and markers were interrogated. STF-31 treatment did not affect cardiomyocyte spontaneous contractility (data not shown). A pulse treatment with STF-31 did not affect abundance of cardiac markers TNNI3 and IRX4 as measured by flow cytometry (FIG. 2C) and treated cardiomyocytes maintained comparable structural organization of TNNT2, which is found in cardiac sarcomeres, (FIG. 2D) 72 hours after treatment initiation. Expression of cardiac genes as measured by q-PCR was not significantly altered after initiation of STF-31 treatment (FIG. 2E).

To confirm selective toxicity in the presence of differentiated cells, colony formation assays were performed with titrating amounts of hiPSC with either day 10 cardiomyocytes (FIG. 2F) or human fibroblasts (FIG. 2G). Initially, a 24-hour pulse treatment was used and resulted in elimination of a majority of hiPSC colonies from day 10 cardiomyocytes, however some colonies remained after treatment (FIG. 5C). A 48 hour pulse treatment with 5 µM STF-31 was found to completely eliminate hiPSC. Both the fibroblasts and cardiomyocytes remained after treatment and spontaneous contraction was observed in the cardiomyocytes at the time of alkaline phosphatase staining (data not shown) and up to 10 days after treatment initiation (data not shown). Altogether, these findings demonstrate that a pulse treatment with STF-31 is an effective strategy for selective elimination of remnant hPSC across a range of progeny.

Figure 3:
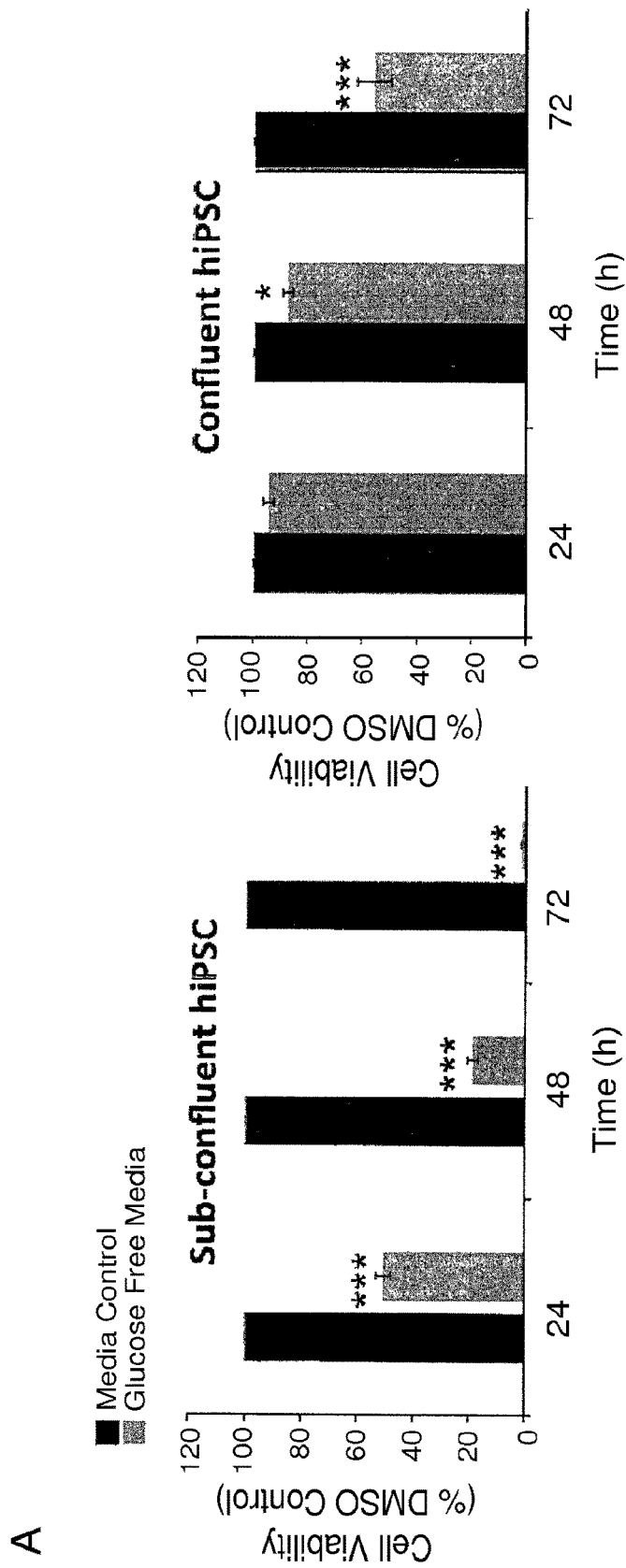
FIG. 3 presents data demonstrating STF-31 inhibits $NAD^+$ salvage pathway. (A) Effect of glucose deprivation on hiPSC (DF6-9-9T) viability as measured by neutral red assay in sub-confluent cells and confluent cells (N=3). (B) ECAR and OCR in hiPSC after treatment with 2.5 µM STF-31 and 30 µM WZB117 (N=3). (C) Bar graphs representing glucose uptake as a percentage of vehicle control for hiPSC treated for 1, 15, 18, and 24 hours with 2.5 µM STF-31, 30 µM WZB117, and 20 µM cytochalasin B in E8 media (N=3). (D) Representative immunoblots for total and cleaved caspase-9, cleaved caspase-3, and GAPDH in sub-confluent hiPSC treated with glucose deprivation, 30 µM WZB117, or 2.5 µM STF-31. hiPSC were treated for 3 hours with 1 µM camptothecin as a positive control for immunoblotting. (E) Nucleotide levels in hiPSC after treatment with 20 mM 2-DG for 24 h or 2.5 µM STF-31 for 3-24 h (N=3). (F) hiPSC viability as measured by neutral red assay in cells treated with STF-31 alone or in the presence of 1 or 10 µM nicotinic acid (N=3). Above each bar are representative brightfield images illustrating cell density and morphology for 48-hour treatment in each condition. Data are represented as mean±SEM. * $p \leq 0.05$, *** $p \leq 0.001$ compared to media or DMSO control.
Figure 3:
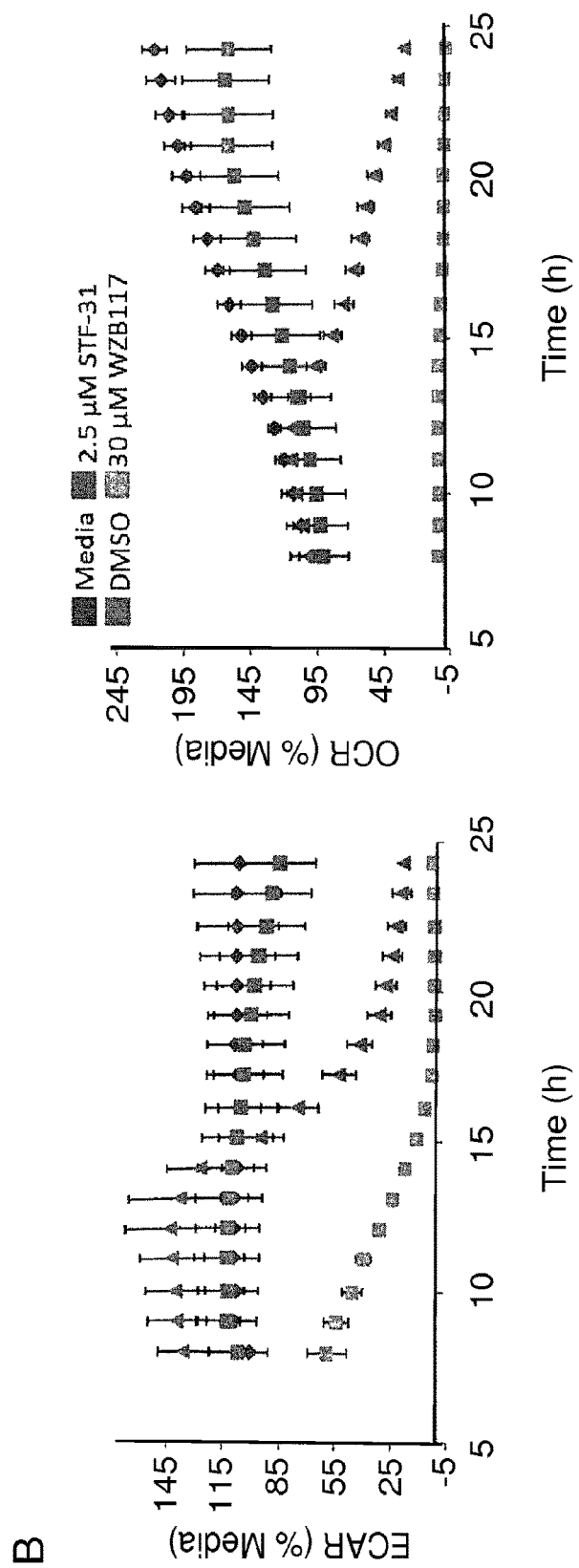
Figure 3:
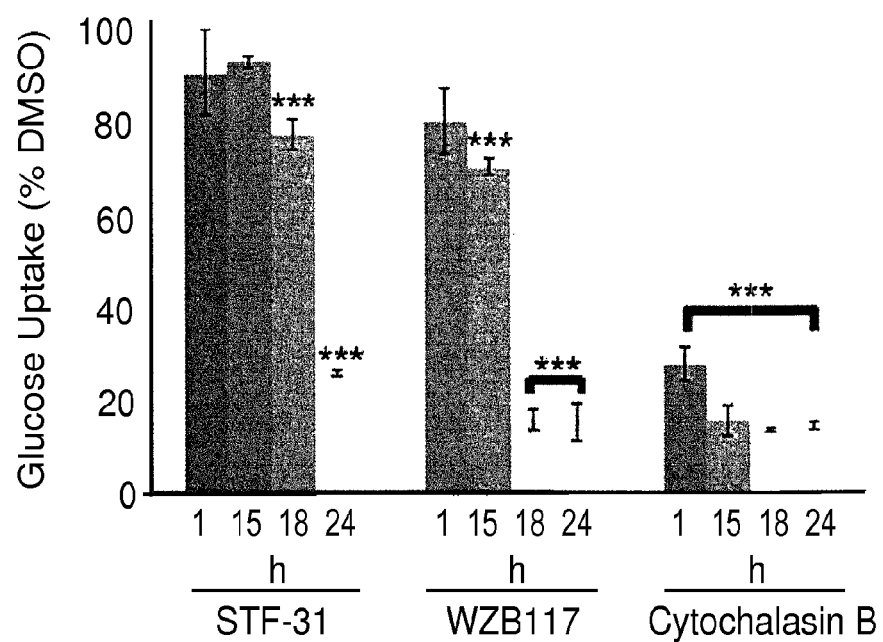
Figure 3:
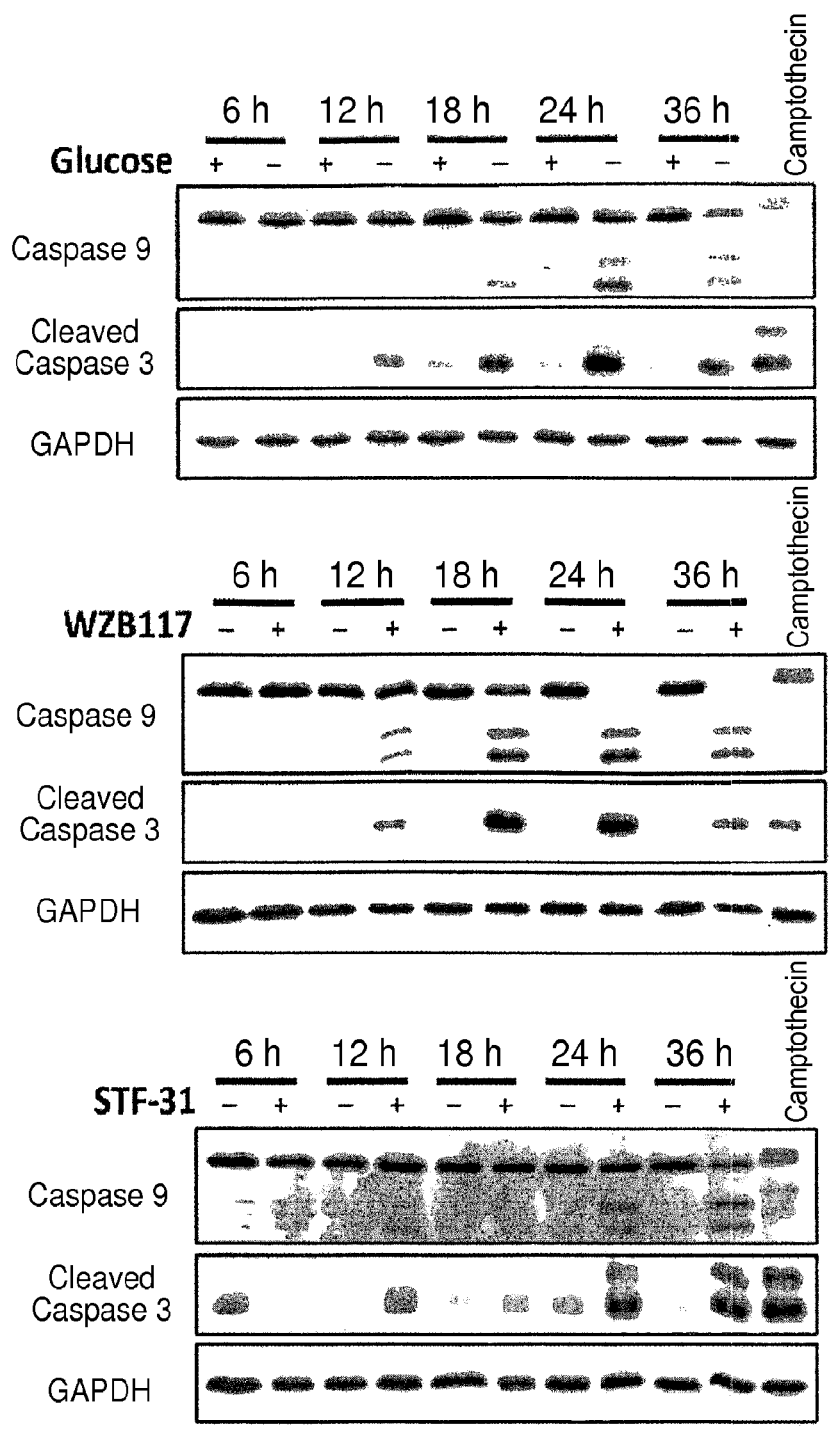
Figure 3:
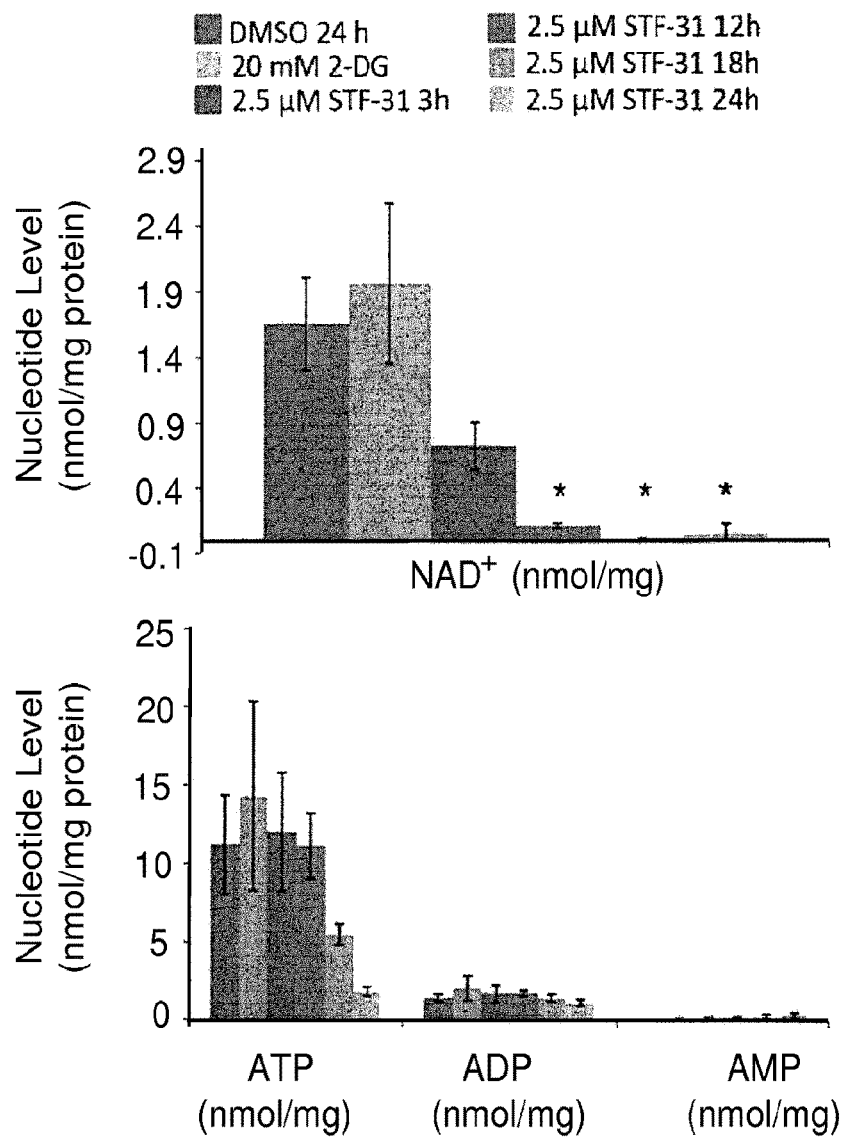
Figure 3:
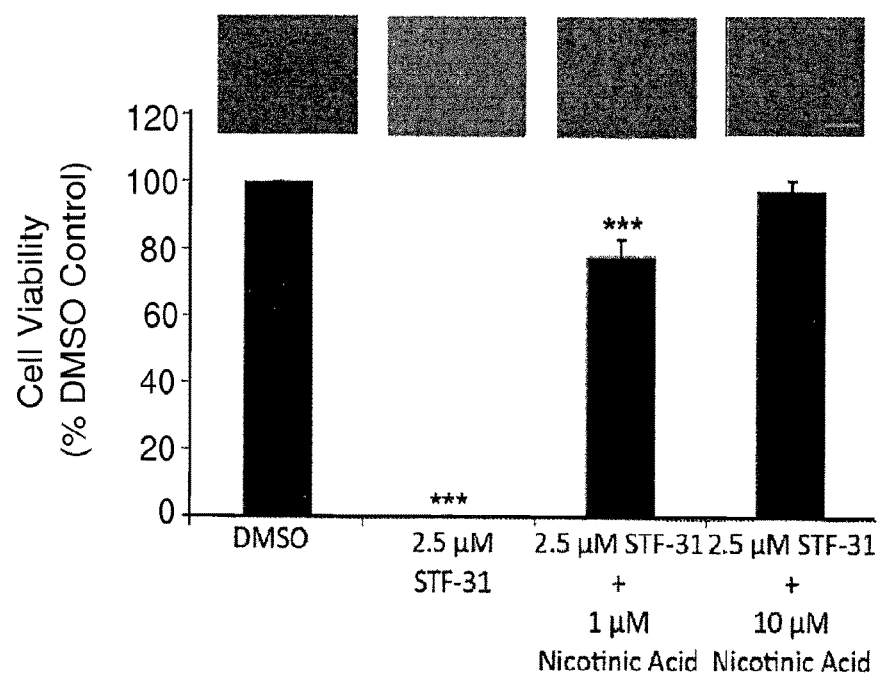
Figure 7:
FIG. 7 demonstrates the effects of glucose deprivation, STF-31, and WZB117 on metabolic flux and expression of apoptosis markers. (A) ECAR and OCR in hiPSC (DF6-9-9T) treated with 20 mM 2-deoxy-d-glucose (2-DG). (B) Representative immunoblots for p-AMPK and AMPK levels in sub-confluent hiPSC treated for 6-36 hours with glucose deprivation, 30 µM WZB117, and 2.5 µM STF-31 (N=3). (C) Bar graph representing caspase-3/7 activity in sub-confluent hiPSC treated with 2.5 µM STF-31, 30 µM WZB117, and glucose deprivation for 6-24 hours as measured by a fluorescence based caspase-3/7 activity. * $p \leq 0.05$, *** $p \leq 0.001$ compared to media or DMSO control.
Figure 7:
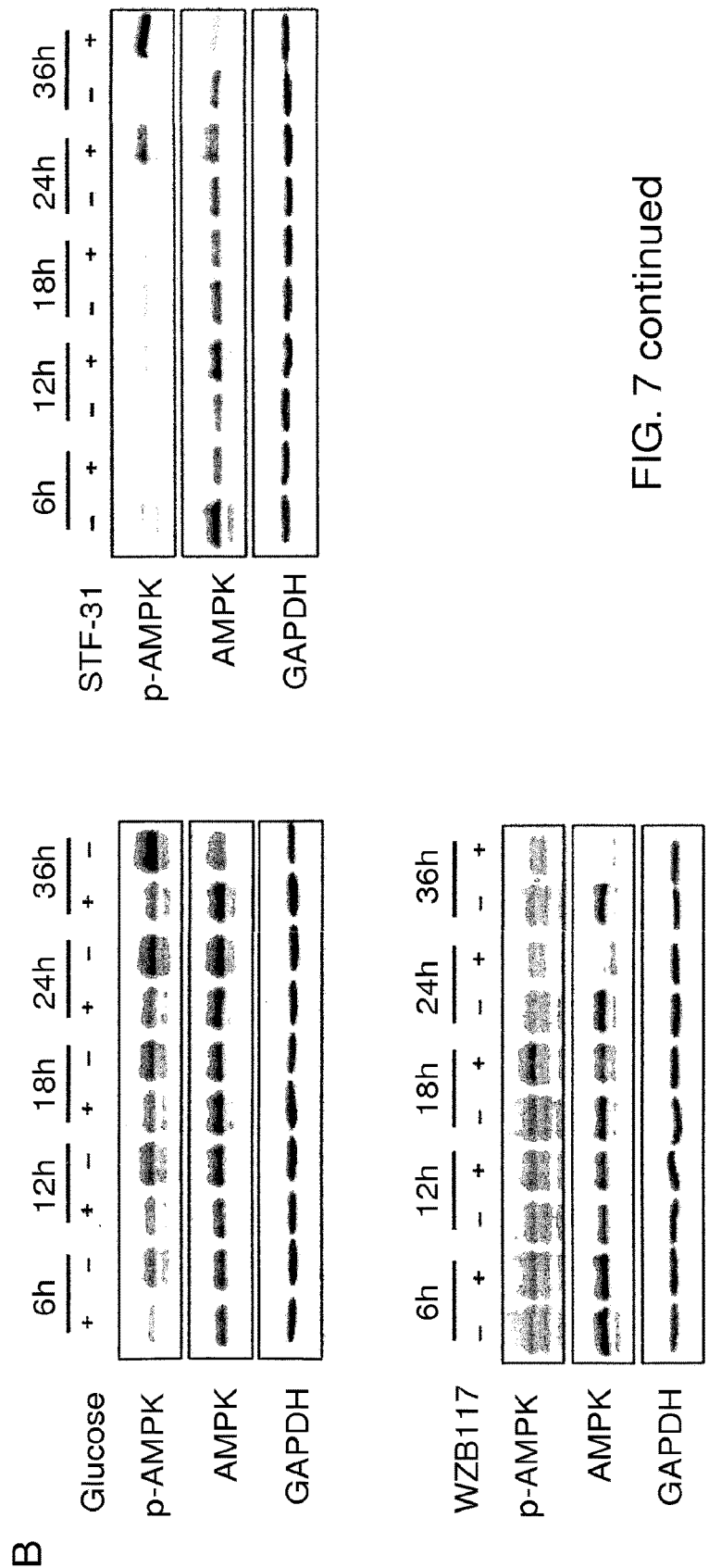
Figure 7:
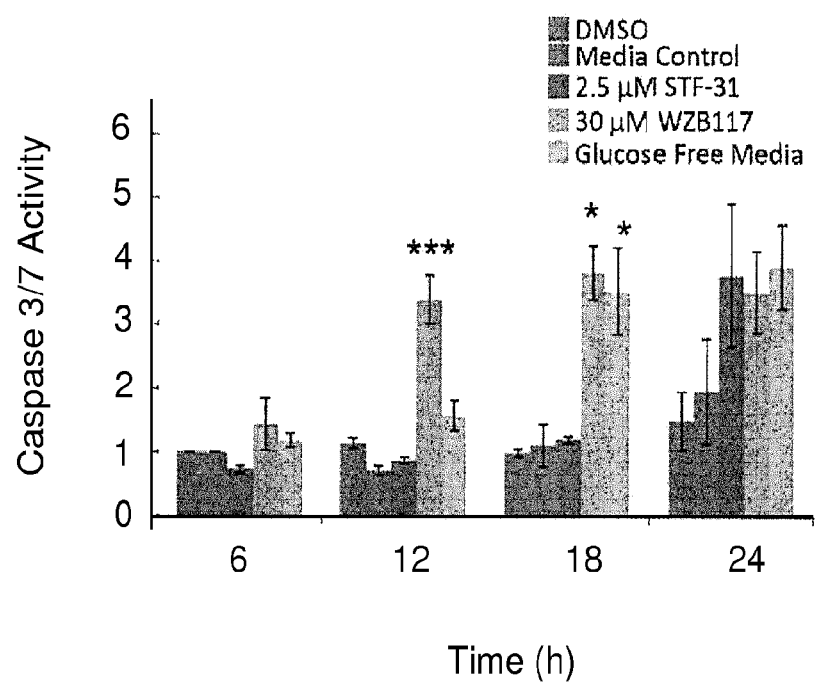
Figure 7:
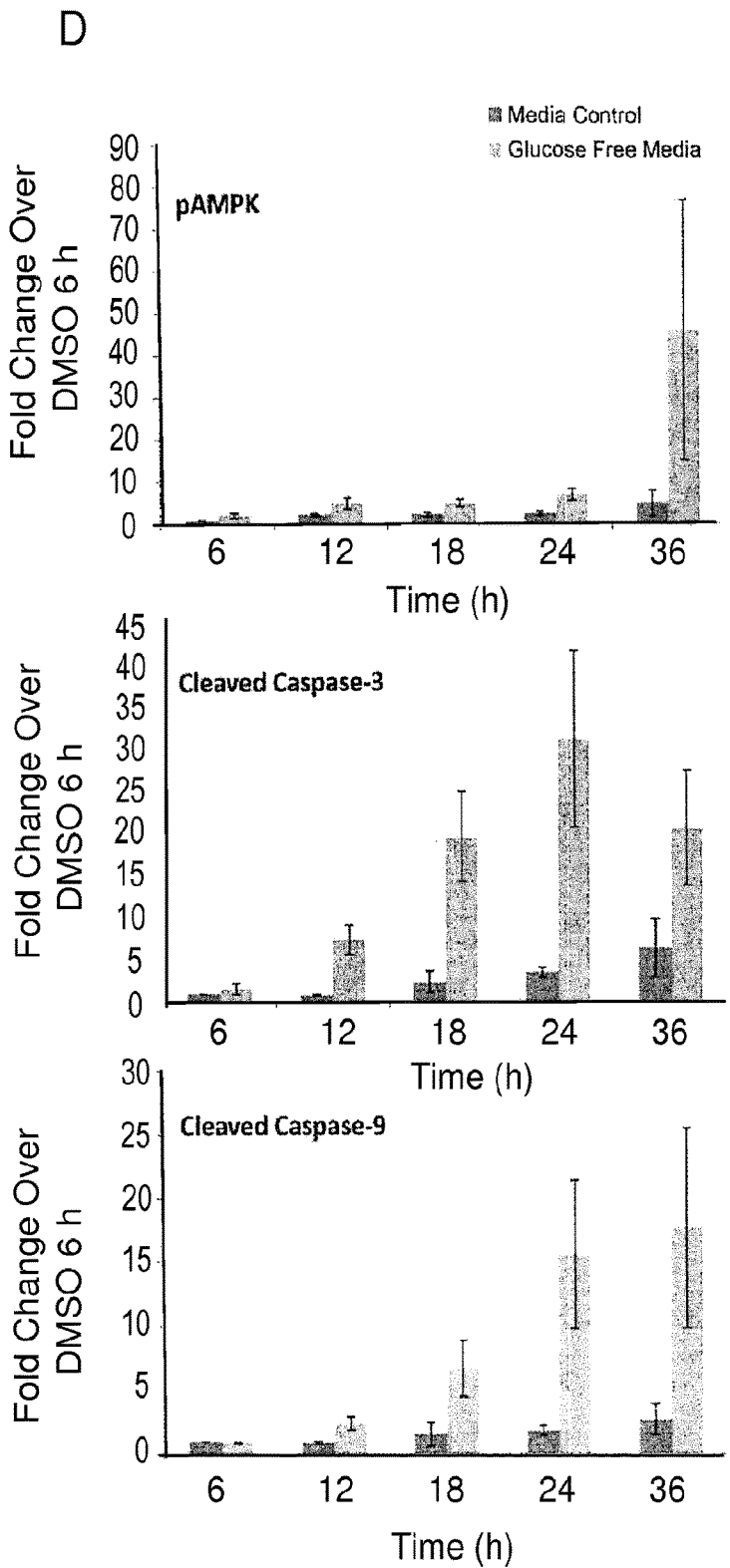
Figure 7:
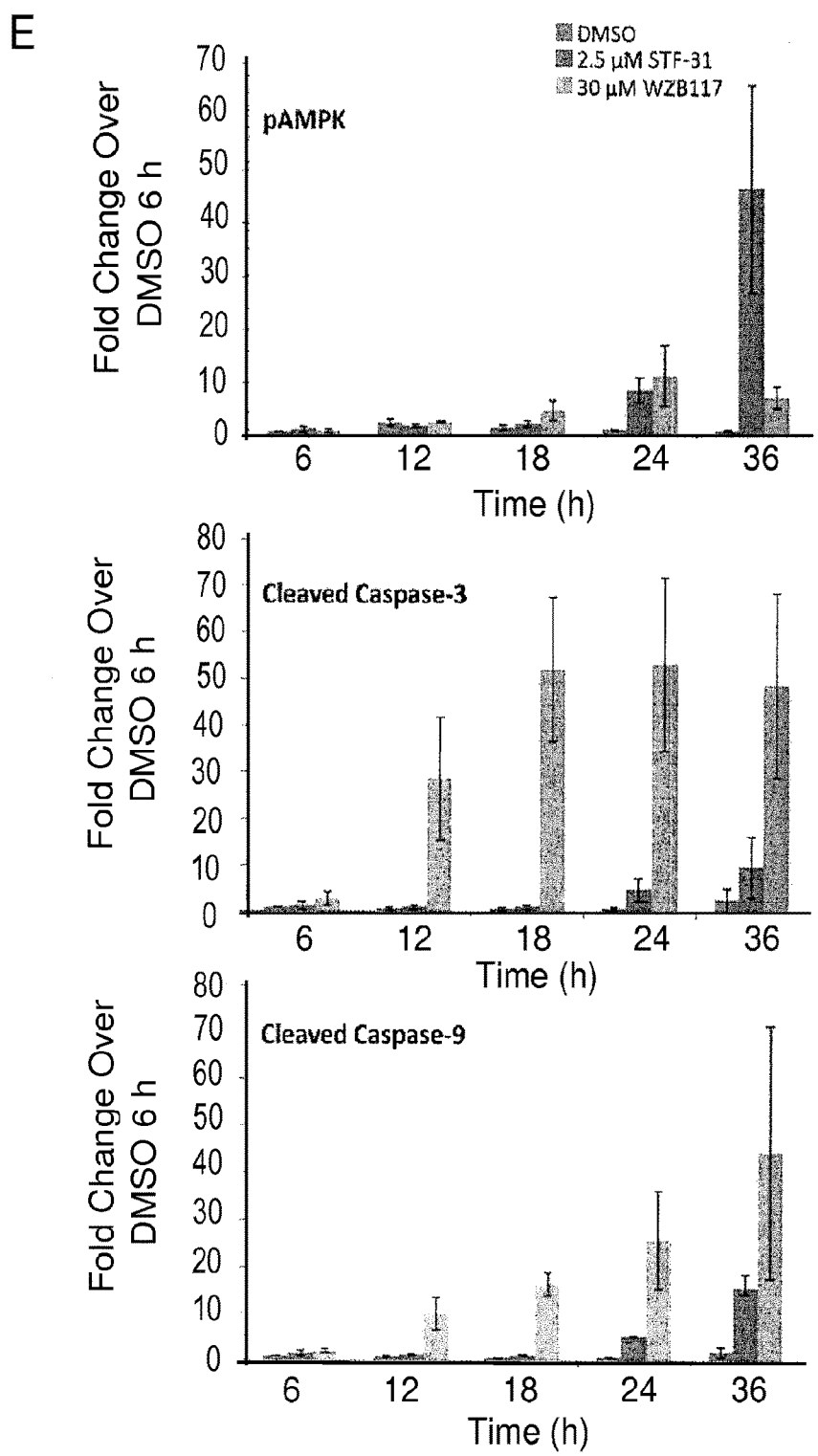

In cancer cells, STF-31 was initially described as a GLUT1 inhibitor that induces necrosis [35]. However, because of the differences in timing and efficacy that we observe between STF-31 and WZB117 (an irreversible GLUT1 inhibitor), we set out to further explore the mechanism of action of STF-31 in hPSC. In these studies, glucose deprivation was used for comparison as it has been previously reported as a method for hPSC elimination [16]. Similar to the results observed for WZB117, glucose deprivation was toxic to sub-confluent cells, but toxicity was both delayed and decreased in confluent cells (FIG. 3A). Using extracellular flux analysis, the extracellular acidification rate (ECAR) was measured to provide information on glycolysis and oxygen consumption rate (OCR) was monitored to probe mitochondrial respiration. Treatment of hiPSC with the GLUT1 inhibitor WZB117 led to a decrease in ECAR by the earliest timepoint measured (FIG. 3B), acting in a manner similar to that observed with 2-deoxyglucose (2-DG), an inhibitor of glucose metabolism (FIG. 7A). In contrast, the decrease in ECAR following STF-31 treatment was significantly delayed by up to 15 hours as compared to the inhibitors of glucose oxidation (FIG. 3B). Results for OCR are similar to ECAR, as hiPSC treated with STF-31 required 15 h before reductions in OCR were observed. This finding is in contrast to the effects of WZB117, which decreased OCR by the first time point examined (8 hours) (FIG. 3B).

Consistent with the effects on glucose metabolism, STF-31 did not alter glucose uptake in hiPSC following 1 hour of treatment, while 1 hour treatment with WZB117 resulted in a 20% decrease in uptake (FIG. 3C). The first time point at which STF-31 caused a decrease in glucose uptake was 18 hours after treatment, which was 3 hours after the decrease in ECAR. Thus, the significant decrease in glucose uptake that is consistent with results previously reported in cancer [35] occurred after STF-31-mediated inhibition of glycolysis and mitochondrial oxidative metabolism. The delayed effects of STF-31 on glucose uptake were unexpected for an inhibitor affecting either glucose transport or GLUT1 biogenesis and are not consistent with the reported mechanism of action for STF-31 as a GLUT1 inhibitor.

WZB117 and STF-31 have been reported to induce necrosis in cancer cells based on annexin staining at 24-48 hours and 24-72 hours of treatment, respectively, but other reports have associated a decrease in ATP due to glucose starvation with apoptosis [36-38]. To determine how WZB117 and STF-31 promote hiPSC death, effects on energy sensing pathways were examined by measuring phosphorylation of AMP-activated protein kinase (p-AMPK) in sub-confluent cells. In response to WZB117 treatment and glucose deprivation, p-AMPK was detected as early as 12 hours post-treatment and total levels of AMPK decreased by 24 hours following WZB117 treatment of hiPSC (FIG. 7B). In response to STF-31 treatment, there was an increase in p-AMPK at 24 hours, approximately 8 hours after the decrease in ECAR and OCR. The timing of AMPK activation proved distinct between STF-31 and both glucose deprivation and WZB117 treatment. Moreover, in WZB117-treated and glucose-deprived cells, cleaved caspase-3 and -9 were observed at 12 hours and remained elevated until 36 hours, at which time a decrease in cleaved caspase-3 and -9 levels are observed (FIG. 3D). Induction of caspase-3/7 activity was also observed as early as at 12 hours (FIG. 7C). In contrast, STF-31 caused caspase-3 and -9 cleavage significantly later (FIG. 3D) and this coincided with caspase-3/7 activity at 24 hours after initiation of treatment (FIG. 7C). Thus, WZB117 and STF-31 appear to act on hiPSC though activation of caspase-mediated cell death pathways.

Figure 4:
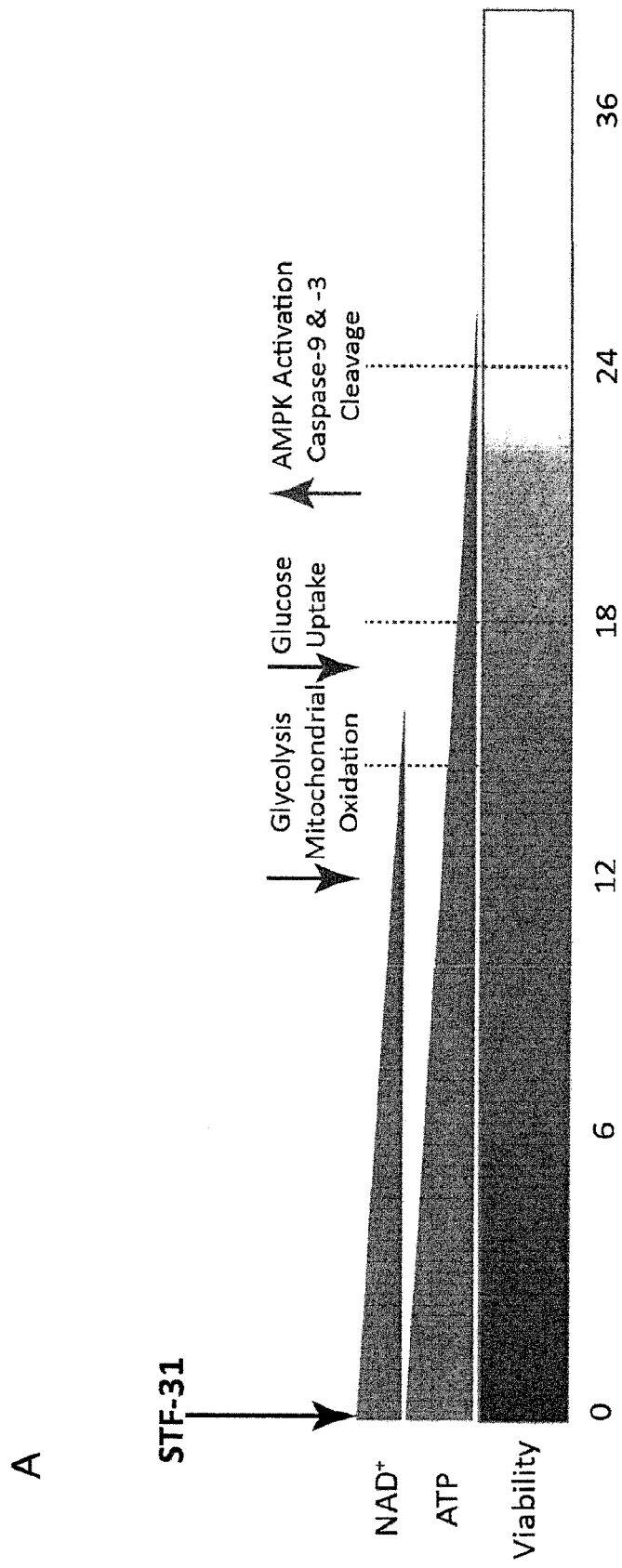
FIG. 4 is a diagram representing temporal effects of treating hPSCs (A) with STF-31 or (B) glycolytic inhibition.
Figure 4:
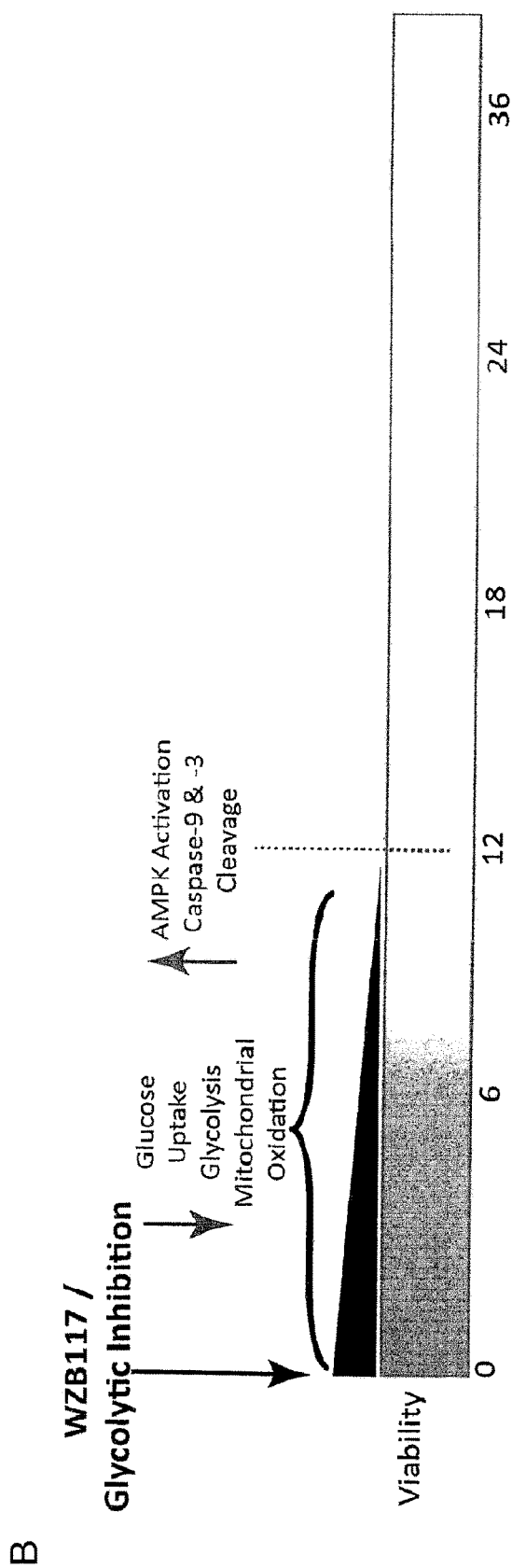

The temporal discordance among metabolism, glucose uptake, and caspase activation (FIG. 4) prompted us to measure adenine and pyridine nucleotide levels because they are known to affect both glycolytic and oxidative metabolism and cell viability [33]. These analyses revealed that with STF-31 treatment, $NAD^+$ levels are reduced to ~50% by 3 hours and to <1% by 18 hours. ATP levels do not decrease until 18 hours (FIG. 3E). These data suggest that STF-31 leads to an inhibition of the $NAD^+$ de novo synthesis or salvage pathways. To investigate which $NAD^+$ pathway is being targeted, rescue experiments were performed using metabolites added in the presence of STF-31. The addition of 1 and 10 µM nicotinic acid restored hPSC viability to 78% and 97%, respectively (FIG. 3F). Nicotinic acid is normally not present in hPSC culturing conditions and can be utilized by nicotinic acid phosphoribosyltransferase (NAPRT) in one of the three $NAD^+$ salvage pathways. Alternatively, the addition of 10 and 100 µM nicotinamide, the substrate for nicotinamide phosphoribosyltransferase (NAMPT), failed to rescue STF-31 mediated toxicity (data not shown). Altogether, these data suggest that STF-31 inhibits the NAMPT dependent $NAD^+$ salvage pathway.

Figure 8:
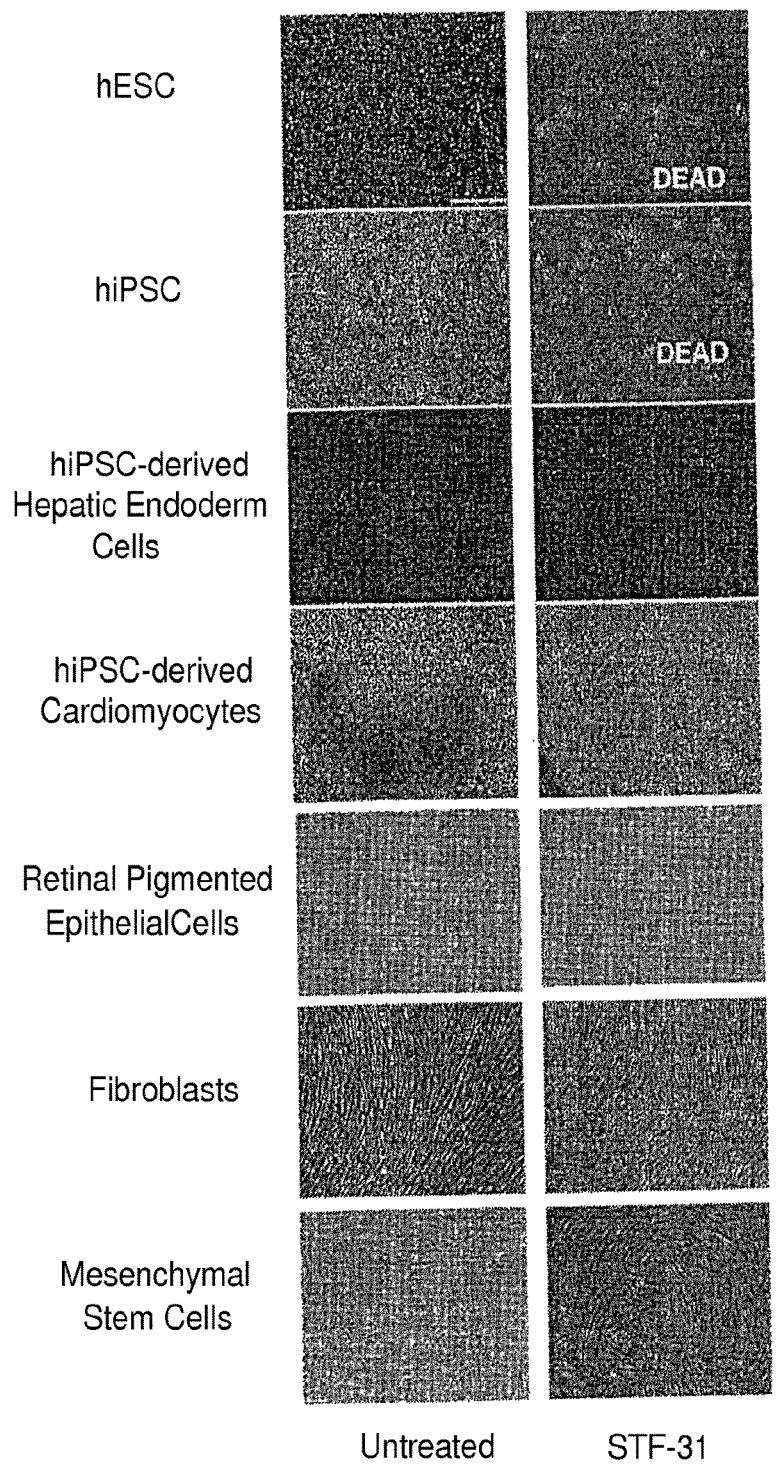
FIG. 8 demonstrates that STF-31 is toxic to pluripotent stem cells, but hiPSC-derived progeny and terminally differentiated cells are resistant to STF-31 toxicity. (A) Phase contrast images of hESCs, hiPSCs, and differentiated cells upon STF-31 treatment (2.5 µM for 72 hours). (B) Human iPSC-derived cardiomyocytes were treated on day 10 of differentiation with 2.5 µM STF-31, and protein and mRNA levels for cardiomyocyte markers were assessed 72 hours later by flow cytometry (top), immunofluorescence (middle), and 24-72 hours later by qRT-PCR (bottom). (C) Human iPSC-derived neural progenitors were treated with 2.5 µM for 72 hours and assessed by MTT assay (top; day 10 and day 12 progenitors) and immunofluorescence (bottom; day 12 progenitors shown). In all cases, STF-31-treated cardiomyocytes and progenitor cells were indistinguishable from controls.
Figure 8:
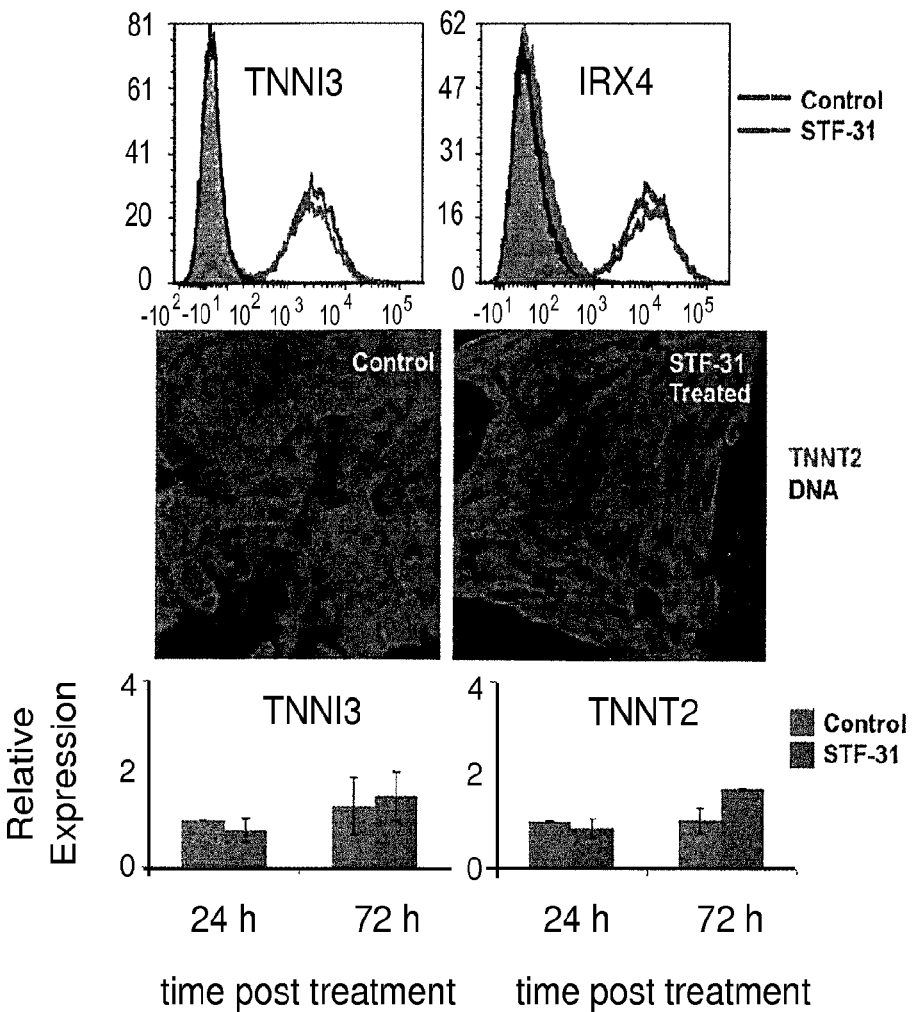
Figure 8:
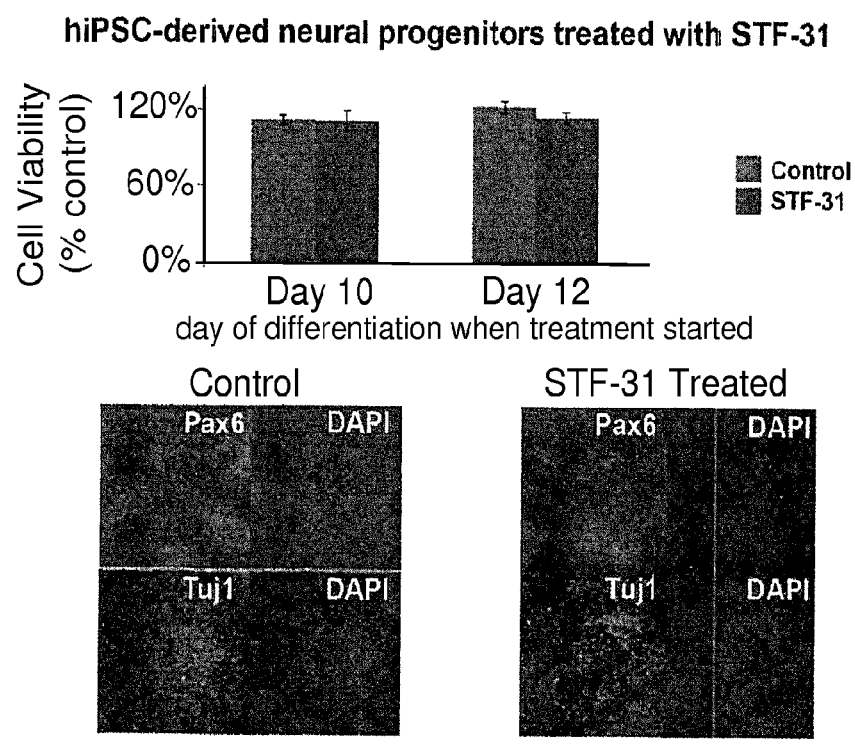

To assess STF-31's toxicity to hiPSC-derived progeny and terminally differentiated cells, we cultured mesenchymal stem cells, fibroblasts, retinal pigmented epithelial cells, hiPSC-derived cardiomyocytes, specified hepatic endoderm cells, and neural progenitors in the presence of STF-31. None of these cell types exhibited visible changes in morphology or obvious cell death with STF-31 treatment (FIG. 8A). Viability measurements were consistent with these visual observations. See data for cardiomyocytes, neural progenitors, and fibroblasts in FIGS. 8B-C). Importantly, cardiomyocytes treated with STF-31 on day 5 (progenitor) and day 10 (committed; not terminally differentiated) of differentiation exhibit spontaneous rhythmic contractions, protein and mRNA levels of cardiomyocyte markers, and structural features indistinguishable from controls (data for cells treated on day 10 in FIG. 8B). See Boheler et al., *Stem Cell Reports* 3, 185-203 (2014). Altogether, these findings suggest STF-31 is suitable for a wide range of hPSC derivatives.

This study establishes and defines an effective strategy for selectively toxicity of hPSC. Pluripotent stem cell metabolism is characterized by aerobic glycolysis, decreased mitochondrial membrane potential, and increased reliance on anabolic processes [39]. Enhanced expression of GLUT1 and reliance on glycolytic metabolism make glucose deprivation [16] or inhibition of GLUT1 promising strategies for selective elimination of hPSC as we previously described. See Boheler et al., *Stem Cell Reports* 3, 185-203 (2014).

However, in our culture system, we found that glucose deprivation, WZB117, and PluriSIn had limited to no toxicity on confluent monolayers of hPSC, an observation that was consistent among five hPSC lines and two different media compositions. Therefore, these strategies may not be ideal for applications that require confluent cell monolayers or altered proliferation rates derived from hPSC, such as cardiomyocytes, hepatocytes, and neuronal cultures [19, 22, 24, 34].

We show that hPSC can be selectively targeted using STF-31, which offers ideal toxicity characteristics for culture systems that require confluent monolayers of cells for differentiation or produce confluent monolayers of differentiated cells. Regenerative medicine strategies that require tissues, scaffolds, or other three-dimensional cell products should therefore benefit from these findings. STF-31 offers advantages over current approaches as it exhibits continued toxicity after a 24 or 48 hours pulse treatment. This toxicity is independent of cell density and provides for a 22-fold difference between the $LD_{50}$ of confluent hPSC and hPSC-derived cardiomyocytes. Moreover, treatment of a co-culture with cardiomyocytes and hiPSC provided selective elimination of the hPSC, while sparing cardiomyocytes. Finally, 5 µM STF-31 was sufficient to prevent hPSC colony self-renewal and regrowth for 7 days in vitro; however, the traditional colony formation assay that involves dissociation and re-plating of hPSC indicates lower concentrations of STF-31 may also be effective.

STF-31 has been reported to inhibit GLUT1 in cancer cells [35] and is currently marketed as a GLUT1 inhibitor. However, our data for STF-31-mediated toxicity and effects on metabolic flux do not support this mechanism of action. Rather, these data show that the effects on glycolytic metabolism are due to depletion of $NAD^+$. STF-31-mediated temporal effects on metabolism (glycolysis and oxidative phosphorylation) differ from both glucose deprivation and WZB117. Additionally, the failure to block glucose uptake prior to inhibition of glycolytic flux demonstrates that STF-31-mediated toxicity in hPSC is not due to GLUT1 inhibition. As a result of these findings, we set out to define the mechanism of action of STF-31. Our data reveal that STF-31 targets NAMPT, the enzyme that catalyzes the rate-limiting step in the conversion of nicotinamide to $NAD^+$ in one of the $NAD^+$ salvage pathways. Further support of this mechanism is found in a separate study that was published while our manuscript was being prepared. Dragovich et al. systematically synthesized 67 different 3-aminopyridine-derived amides and screened them for their ability to inhibit NAMPT [40]. From this screen, Compound 51, which has the same chemical structure as STF-31, was found to directly inhibit NAMPT in a purified enzyme assay ($IC_{50}$=19 nM). By X-ray crystallography, STF-31 was shown to bind in the ligand binding pocket of NAMPT. Altogether, these data confirm that STF-31 mediated toxicity is caused by inhibition of an $NAD^+$ salvage pathway by targeting NAMPT. Additionally, our study provides evidence that the toxic effects mediated by STF-31 in hPSC can be attributed to depletion of $NAD^+$, not inhibition of glucose transport. This discovery provides fundamental insight into the basic metabolic profile of pluripotency, as these cells are less able to compensate for a loss of $NAD^+$ salvage pathways than their differentiated progeny. The reliance on $NAD^+$ salvage pathways shown here is consistent with a recent report that used compound FK866 to inhibit NAMPT and showed that adequate $NAD^+$ levels are required to establish and maintain pluripotency during reprogramming [41]. However, the report by Son et al., did not demonstrate complete cell death of hPSC in the conditions tested. Going forward, more potent and water-soluble inhibitors of NAMPT should be important reagents for the preparation of clinically relevant cells and tissues derived from hPSC.

In summary, this study establishes that targeting the $NAD^+$ salvage pathway mediated by NAMPT represents an effective and efficient strategy for selective hPSC toxicity. Our detailed analyses of the cellular metabolic events further support the use of NAMPT inhibitors over glucose starvation or GLUT1 inhibition for the elimination of hPSC in culture. When using STF-31 to inhibit NAMPT in a 24 or 48 hours pulse treatment scheme, hPSC elimination can be achieved across many culture conditions without cytotoxic effects on the terminally differentiated cells and hPSC-derived progeny tested in this study.

Materials and Experimental Procedures:

Cell Culture and Reagents:

hiPSC (DF6-9-9T, KB3 [19, 20]) and hESC (H1, H7, H9 [21]) were cultivated in monolayer culture on Matrigel in E8 or mTeSR medium as previously described [6, 19]. For all experiments, hPSC were plated at 1.5e5 total cells per 2 $cm^2$, unless otherwise specified, as plating an explicit number of cells during routine passaging enhances reproducibility among experiments and maintains high quality monolayer cultures of pluripotent cells. Treatment with small molecule inhibitors was initiated between 24 and 96 hours post-plating. These time points represent the time at which cells are typically 15-20% and 100% confluent, respectively. hiPSC derived cardiomyocytes were differentiated and maintained as previously described [22]. For hESC colonies that were grown on a feeder cell layer, H1 colonies were cultured on mitotically inactivated human fibroblast feeders in E8 media, colonies were passaged with collagenase IV for 40 min at 37° C. [23]. PAX6-positive neuronal progenitors were differentiated as described [24]. Human fibroblasts were cultured as previously described [19]. Small molecules STF-31 (4-[[[[4-(1,1-Dimethylethyl)phenyl]sulfonyl]amino]methyl]-N-3-pyridinylbenzamide, Tocris), WZB117 (EMD Millipore), PluriSIn (Sigma-Aldrich), nicotinic acid (Sigma-Aldrich), and nicotinamide (Sigma-Aldrich) were used to treat cells. For glucose deprivation, E8 media was prepared as described [19] with the modification that DMEM F-12 without glucose (US Biological) was used. For glucose deprivation media control, 17.5 mM glucose (Sigma-Aldrich) was added into glucose free E8 media.

In Vitro Toxicity Assays:

Treatment with small molecules or glucose deprivation was initiated in hESC or hiPSC at 24 and 96 h post-plating and in vitro toxicity assays were performed at specified treatment endpoints 24-96 hours after treatment initiation. For pulsed treatment, hiPSC were treated with STF-31 for 24 hours, washed twice with D-PBS, and cultured in media for an additional 48 hours. Neutral red assays for cell viability were performed as previously described [25]. In vitro cell death was determined using SYTOX® Green nucleic acid stain (Life Technologies). Briefly, cells were incubated in 5 µM SYTOX® Green for 30 minutes at 37° C. in a humidified cell incubator with 5% $CO_2$. Percent cell viability was determined by normalizing to replicate cells incubated with 120 µM digitonin (Sigma-Aldrich) and 5 µM SYTOX® Green. Imaging of cell viability was performed using Live/Dead® Viability/Cytotoxicity Kit, for mammalian cells (Life Technologies). Cells were stained for 20 minutes at room temperature with 4 µM Calcein AM to detect viable cells and 2 µM Ethidium Homodimer 1 to detect cells with compromised membranes. Representative images of alterations in cell morphology were acquired on confluent hPSC 24-72 hours after treatment initiation. Imaging was performed with a Nikon Ti-U inverted microscope.

BrdU Incorporation and Flow Cytometry:

Cells were plated at 7.5e5 cells per 9.6 cm² and 10 µM 5-bromo-2-deoxyuridine (BrdU) was incorporated in hiPSC 24-96 h post-plating for 1 hour at 37° C. in a humidified cell incubator with 5% $CO_2$. After incorporation, cells were collected and stained using FITC BrdU Flow Kit per manufacturer's guidelines (BD Biosciences). Cell viability was determined using Fixable Viability Dye eFluor® 450 (eBiosciences). Analyses were performed on 30,000 events acquired on a BD LSRII flow cytometer (BD Biosciences), using FCSExpress V3 (DeNovo Software). The percent of cells in each phase of the cell cycle was determined by gating on populations within each phase in the live cell population.

Colony Formation Assay:

The colony formation assay was performed in three different variations on confluent hiPSC that were treated with 2.5 and 5 µM STF-31, 30 µM WZB117, 20 µM PluriSIn for 24 hours. The first iteration was adapted from previously described method [26], after 24 hours of treatment, hiPSC were detached with Accutase (StemCell Technologies), resuspended in E8, passed though 12×75 mm tube with cell strainer cap (Falcon), and plated at 5e4 live cells per 2 cm². Media were changed every 48 hours and cells were cultured for six days, at which time staining for alkaline phosphatase was performed with leukocyte alkaline phosphatase kit (Sigma-Aldrich) as described [27] and plates were visually inspected for phosphatase-positive colonies. This strategy represents the most common implementation of the colony formation assay. However, concerns regarding the cell death normally encountered during passaging prompted another approach for stricter assessment. In the second iteration, cells were treated for 24 hours, washed twice with 0.5 mL D-PBS, and media refreshed with E8. Thereafter, media were replaced daily for six days at which point staining for alkaline phosphatase activity was performed. In this version, cells do not undergo the stress of passaging, which may result in erroneously low viability that is not a direct result of the compound; thus, this modified assay is considered a more stringent assessment of hPSC elimination than the former. Elimination of hiPSC from co-cultures with differentiated cells was performed with human fibroblasts and day 10 cardiomyocytes derived from hiPSC. hiPSC (DF6-9-9T) were plated at concentrations ranging from 100-10,000 live cells per well with human fibroblasts (1.75e5 cells) or day 10 differentiated cardiomyocytes (3.75e5 cells) in E8 and Y-27632 per 9.6 cm². After 24 hours, treatment was performed with 5 µM STF-31 for 24 or 48 hours, washed twice and media refreshed daily with E8. Six days after plating, staining for alkaline phosphatase activity was performed. For elimination of hESC colonies grown on mitotically inactivated human fibroblast feeders, colonies were treated for 96 hours with 2.5 µM STF-31 at which point cells were imaged with brightfield microscopy and stained for alkaline phosphatase activity or colonies were passaged with collagenase IV (2 mg/mL for 40 minutes at 37° C.) and cultured for an additional 72 hours and stained for alkaline phosphatase activity. Imaging of wells was performed with a Sony Cyber-shot DSC-TX30 and individual colonies with a Nikon stereoscope.

Characterization of Cardiomyocytes:

For all experiments, a 24-hour pulse treatment with 5 µM STF-31 was performed on day 10 cardiomyocyte differentiation cultures derived from hiPSC (DF6-9-9T). Flow cytometry was performed as previously described 72 hours after initiation of STF-31 treatment for Troponin I type 3 (TNNI3) and Iroquois-class homeodomain protein (IRX4) [19]. Quantitative-real time PCR for TNNI3, Troponin T2 (TNNT2), and Homeobox protein Nkx-2.5 (NKX2-5) was performed as previously described using Taqman® Assays [19] (Life Technologies) 24-72 hours after initiation of STF-31 treatment. For immunoflourescent detection of TNNT2, cardiomyocytes were passaged onto coverslips 72 h after initiation of STF-31 treatment and cultured for an additional 48 hours. Cells were then fixed with 4% paraformaldehyde, permeabilized with 0.2% Triton-X, incubated with primary antibody for Troponin T (TNNT2) (Abcam: ab8295) overnight at 4° C. Cells were then incubated in secondary antibody goat anti-mouse IgG1-Alexa 568 (Life Tech: A-21124) and nuclei were detected with Hoechst 33342 (Life Tech: H21492). Cells were imaged with a Nikon Ti-U inverted microscope and Nikon Eclipse 90i confocal microscope.

Extracellular Flux Analysis:

hiPSC were plated at 6e4 cells per well on specialized microplate (Seahorse Bioscience) as previously described [28] with several exceptions. Extracellular flux analysis was performed on hiPSC 48 hours post-plating using Seahorse Bioscience XF24 Analyzer. Cells were treated with 2.5 µM STF-31, 30 µM WZB117, 20 mM 2-deoxyglucose (2-DG; Sigma-Aldrich), vehicle control, or media control for 5.5 h, washed twice with 750 µL assay medium, and placed in 750 µL assay medium containing the appropriate treatment. The microplate was equilibrated in non-$CO_2$ incubator for 1.5 h, and analyzed for 16 h in Seahorse Bioscience XF24 Analyzer. Assay medium consists of basal E8 reagents with the following exceptions: basal DMEM F-12 without phenol red (Gibco), no sodium bicarbonate, and 2.5 mM GlutaMAX™ (Gibco) and 15 mM Hepes (Gibco). Assay medium was adjusted to pH 7.4 at 37° C. prior to use. Extracellular acidification rate (ECAR) and basal oxygen consumption rate (OCR) were collected approximately every 60 minutes. Treatments were normalized to baseline media control value and are represented as average of three biological replicates.

Glucose Uptake Assay:

Sub-confluent hiPSC (24 hours post-plating) were treated with 2.5 µM STF-31, 30 µM WZB117, 20 µM Cytochalasin B (Sigma-Aldrich), and vehicle control for 1, 15, 18, and 24 hours. For 1 hour treatment, cells were placed in Krebs-Ringer Hepes (KRH) containing treatment at 37° C. in a humidified cell incubator with 5% $CO_2$. For 15, 18, and 24 hour treatments, cells were treated in E8 medium for 14, 17, and 23 hours, respectively, at which point media was changed to KRH buffer containing specific treatment for 1 hour. After specified treatment time, glucose uptake was performed with 0.5 µCi [$^3$H] 2-deoxyglucose for 5 min at 37° C. as previously described [29]. Uptake data were normalized to protein concentration measured with Lowry method.

Immunoblot Analysis:

Non-adherent cells were collected by centrifugation, adherent cells were washed once with d-PBS and lysed in Laemmli buffer, combined with non-adherent cell pellet, and heated at 95° C. for 5 minutes. Protein concentration was measured using the Qubit protein assay (Life Technologies). 25 µg of total protein was separated by SDS-PAGE, transferred to nitrocellulose membrane (GE Healthcare Life Sciences) and blocked according to the manufacturer's instructions. Membranes were incubated overnight at 4° C. with the following dilutions of primary antibodies: rabbit anti-cleaved caspase-3 (1:500), rabbit anti-caspase-9 (1:1000), rabbit anti-phospho-AMPK (1:1000), and rabbit anti-AMPK (1:1,000) from Cell Signaling Technology, and mouse anti-GAPDH (1:10,000) from Life Technologies. Membranes were then incubated with secondary antibodies for 45 minutes at the following concentrations: donkey anti-mouse-horseradish peroxidase (1:5,000) and donkey anti-rabbit-horseradish peroxidase (1:7,000) from Jackson Immunoresearch Laboratories, Inc., followed by detection using enhanced chemiluminescence [30].

Cleaved Caspase-3/7 Fluorescence Based Assay:

Treatment with 2.5 µM STF-31, 30 µM WZB117, or glucose deprivation was initiated in sub-confluent hiPSC (24 hours post-plating) for 6, 12, 18, and 24 hours at which time cleaved caspase-3/7 activity was measured as previously described [31, 32] with the following exceptions: cells were cultured in 500 µL E8 media and 250 µL of 3× caspase buffer was added to media at endpoint.

Nucleotide Pool Measurements:

ATP, ADP, AMP, and $NAD^+$ were extracted using perchloric acid precipitation and analyzed using HPLC, following a previously published method [33]. ATP, ADP, AMP and $NAD^+$ peaks were measured for each sample, compared with the standards, and normalized to protein levels.

Statistical Analysis:

All experiments were performed in a minimum of three biological replicates. Data are represented as mean with standard error of the mean for N biological replicates. Statistical analysis was performed using one-way ANOVA with Tukey post hoc test.

References

1. Chong, J. J., et al., *Human embryonic-stem-cell-derived cardiomyocytes regenerate non-human primate hearts*. Nature, 2014.
2. Ebert, A. D., P. Liang, and J. C. Wu, *Induced pluripotent stem cells as a disease modeling and drug screening platform*. J Cardiovasc Pharmacol, 2012. 60(4): p. 408-16.
3. Grskovic, M., et al., *Induced pluripotent stem cells—opportunities for disease modelling and drug discovery*. Nat Rev Drug Discov, 2011. 10(12): p. 915-29.
4. Takahashi, K. and S. Yamanaka, *Induced pluripotent stem cells in medicine and biology*. Development, 2013. 140(12): p. 2457-61.
5. Hentze, H., et al., *Teratoma formation by human embryonic stem cells: evaluation of essential parameters for future safety studies*. Stem Cell Res, 2009. 2(3): p. 198-210.
6. Lawrenz, B., et al., *Highly sensitive biosafety model for stem-cell-derived grafts*. Cytotherapy, 2004. 6(3): p. 212-22.
7. Cui, L., et al., *WNT signaling determines tumorigenicity and function of ESC-derived retinal progenitors*. J Clin Invest, 2013. 123(4): p. 1647-61.
8. Doi, D., et al., *Prolonged maturation culture favors a reduction in the tumorigenicity and the dopaminergic function of human ESC-derived neural cells in a primate model of Parkinson's disease*. Stem Cells, 2012. 30(5): p. 935-45.
9. Kroon, E., et al., *Pancreatic endoderm derived from human embryonic stem cells generates glucose-responsive insulin-secreting cells in vivo*. Nat Biotechnol, 2008. 26(4): p. 443-52.
10. Lee, A. S., et al., *Tumorigenicity as a clinical hurdle for pluripotent stem cell therapies*. Nat Med, 2013. 19(8): p. 998-1004.
11. DeFrancesco, L., *Fits and starts for Geron*. Nat Biotechnol, 2009. 27(877).
12. Cao, F., et al., *Molecular imaging of embryonic stem cell misbehavior and suicide gene ablation*. Cloning Stem Cells, 2007. 9(1): p. 107-17.
13. Rong, Z., et al., *A scalable approach to prevent teratoma formation of human embryonic stem cells*. J Biol Chem, 2012. 287(39): p. 32338-45.
14. Ben-David, U., N. Nudel, and N. Benvenisty, *Immunologic and chemical targeting of the tight-junction protein Claudin-6 eliminates tumorigenic human pluripotent stem cells*. Nat Commun, 2013. 4: p. 1992.
15. Tang, C., et al., *An antibody against SSEA-5 glycan on human pluripotent stem cells enables removal of teratoma forming cells*. Nat Biotechnol, 2011. 29(9): p. 829-34.
16. Tohyama, S., et al., *Distinct metabolic flow enables large-scale purification of mouse and human pluripotent stem cell-derived cardiomyocytes*. Cell Stem Cell, 2013. 12(1): p. 127-37.
17. Ben-David, U. and N. Benvenisty, *Chemical ablation of tumor-initiating human pluripotent stem cells*. Nat Protoc, 2014. 9(3): p. 729-40.
18. Ben-David, U., et al., *Selective elimination of human pluripotent stem cells by an oleate synthesis inhibitor discovered in a high-throughput screen*. Cell Stem Cell, 2013. 12(2): p. 167-79.
19. Boheler, K. R., et al., *A human pluripotent stem cell surface N-glycoproteome resource reveals markers, extracellular epitopes, and drug targets*. Stem Cell Reports, 2014. 3(1): p. 185-203.
20. Yu, J., et al., *Human induced pluripotent stem cells free of vector and transgene sequences*. Science, 2009. 324(5928): p. 797-801.
21. Thomson, J. A., et al., *Embryonic stem cell lines derived from human blastocysts*. Science, 1998. 282(5391): p. 1145-7.
22. Bhattacharya, S., et al., *High efficiency differentiation of human pluripotent stem cells to cardiomyocytes and characterization by flow cytometry*. J Vis Exp, 2014(91): p. 52010.
23. Amit, M. and J. Itskovitz-Eldor, *Morphology of Human Embryonic and Induced Pluripotent Stem Cell Colonies Cultured with Feeders*, in *Atlas of Human Pluripotent Stem Cells*, M. Amit and J. Itskovitz-Eldor, Editors. 2012, Humana Press. p. 15-39.
24. Shi, Y., et al., *Human cerebral cortex development from pluripotent stem cells to functional excitatory synapses*. Nat Neurosci, 2012. 15(3): p. 477-86, 51.
25. Repetto, G., A. del Peso, and J. L. Zurita, *Neutral red uptake assay for the estimation of cell viability/cytotoxicity*. Nat Protoc, 2008. 3(7): p. 1125-31.
26. O'Connor, M. D., M. D. Kardel, and C. J. Eaves, *Functional assays for human embryonic stem cell pluripotency*. Methods Mol Biol, 2011. 690: p. 67-80.
27. Rao, S., et al., *Differential roles of Sall4 isoforms in embryonic stem cell pluripotency*. Mol Cell Biol, 2010. 30(22): p. 5364-80.
28. Zhang, J., et al., *Measuring energy metabolism in cultured cells, including human pluripotent stem cells and differentiated cells*. Nat Protoc, 2012. 7(6): p. 1068-85.
29. Yamamoto, N., et al., *Measurement of glucose uptake in cultured cells*. Curr Protoc Pharmacol, 2011. Chapter 12: p. Unit 12 14 1-22.
30. Khan, P., et al., *Luminol-Based Chemiluminescent Signals: Clinical and Non-clinical Application and Future Uses*. Appl Biochem Biotechnol, 2014. 173(2): p. 333-355.

31. Meares, G. P., et al., *AMP-activated protein kinase attenuates nitric oxide-induced beta-cell death*. J Biol Chem, 2010. 285(5): p. 3191-200.
32. Carrasco, R. A., N. B. Stamm, and B. K. Patel, *One-step cellular caspase-3/7 assay*. Biotechniques, 2003. 34(5): p. 1064-7.
33. Broniowska, K. A., et al., *Effect of nitric oxide on naphthoquinone toxicity in endothelial cells: role of bioenergetic dysfunction and poly (ADP-ribose) polymerase activation*. Biochemistry, 2013. 52(25): p. 4364-72.
34. Mallanna, S. K. and S. A. Duncan, *Differentiation of hepatocytes from pluripotent stem cells*. Curr Protoc Stem Cell Biol, 2013. 26: p. Unit 1G4.
35. Chan, D. A., et al., *Targeting GLUT1 and the Warburg effect in renal cell carcinoma by chemical synthetic lethality*. Sci Transl Med, 2011. 3(94): p. 94ra70.
36. Altman, B. J. and J. C. Rathmell, *Metabolic stress in autophagy and cell death pathways*. Cold Spring Harb Perspect Biol, 2012. 4(9): p. a008763.
37. Coloff, J. L., et al., *Akt requires glucose metabolism to suppress puma expression and prevent apoptosis of leukemic T cells*. J Biol Chem, 2011. 286(7): p. 5921-33.
38. Zhao, Y., et al., *Glucose metabolism attenuates p53 and Puma-dependent cell death upon growth factor deprivation*. J Biol Chem, 2008. 283(52): p. 36344-53.
39. Folmes, C. D., et al., *Energy metabolism plasticity enables stemness programs*. Ann N Y Acad Sci, 2012. 1254: p. 82-9.
40. Dragovich, P. S., et al., *Fragment-based design of 3-aminopyridine-derived amides as potent inhibitors of human nicotinamide phosphoribosyltransferase (NAMPT)*. Bioorg Med Chem Lett, 2014. 24(3): p. 954-62.
41. Son, M. J., et al., *Nicotinamide overcomes pluripotency deficits and reprogramming barriers*. Stem Cells, 2013. 31(6): p. 1121-35.

Example 2—FK866 Toxicity to Human Pluripotent Stem Cells

Figure 10:
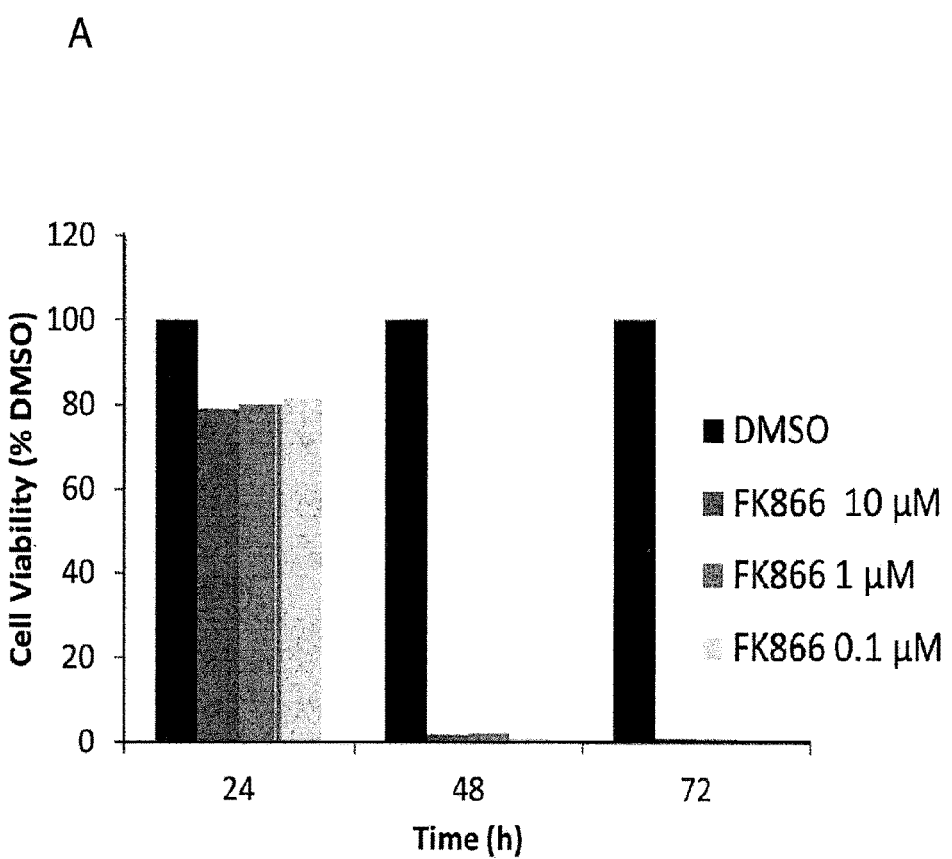
FIG. 10 presents data regarding FK866 toxicity on human pluripotent stem cells. (A) Bar graph demonstrates that FK866 is toxic to human pluripotent stem cells. Cell viability data is presented for hiPSCs treated with FK866 for up to 72 hours. Timing of cell death for this NAMPT inhibitor was similar to that observed for STF-31, independent of concentration. (B) Cell viability of human pluripotent stem cells 72 hours after treatment initiation with FK866. Cells were treated with a range of concentrations (1 nM to 10 µM) either continuously or for 24 hour pulse.
Figure 10:
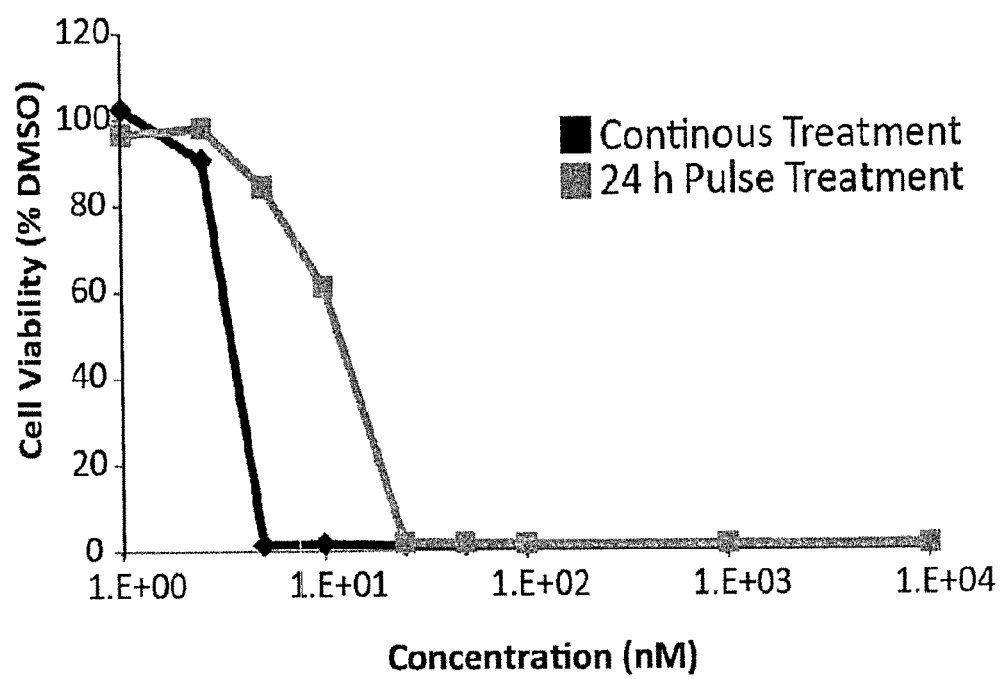

FIG. 10 presents cell viability data for hiPSCs treated with FK866 (FIG. 9B) for up to 72 hours. Timing of pluripotent stem cell death for this NAMPT inhibitor was similar to that observed for STF-31. It was also observed that FK866 was toxic to human pluripotent stem cells at lower concentrations than STF-31. These data suggest that STF-31 and FK866 will be clinically relevant and are consistent with our findings that STF-31 does not affect differentiated progeny in culture. Therefore, an effective strategy for selectively eliminating pluripotent stem cells is to deplete NAD$^+$ levels using a NAMPT inhibitor. Moreover, these data demonstrate that NAMPT inhibition provides a rapid, scalable, and inexpensive method that works independent of media composition, cell density, and cell line—making the strategy more universally applicable than those previously reported. Importantly, as STF-31 and FK866 can reduce cancer mass in vivo, these studies suggest their anti-tumor properties are not limited to pluripotent cells. Thus, these compounds will be useful for selectively eliminating tumorigenic cells in cells prepared for transplantation, independent of whether teratoma-causing cells in differentiated cultures are pluripotent or comprise one or more differentiated phenotypes.

Figure 11:
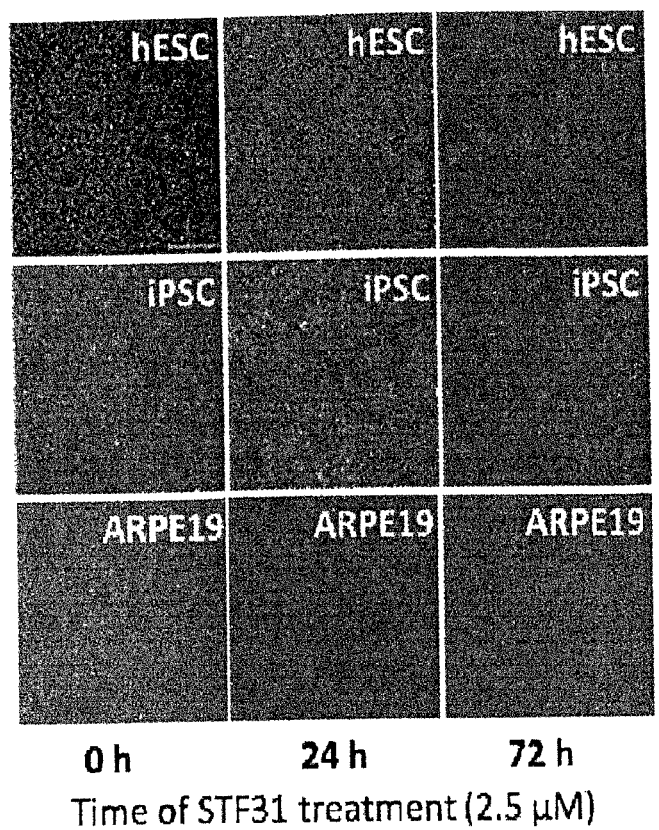
FIG. 11 presents data demonstrating adult pigmented retinal epithelial cells (ARPE) and PAX6 positive neural progenitor cells are resistant to STF-31 treatment. (A) Brightfield images of human embryonic stem cells (hESC), human induced pluripotent stem cells (hiPSC), and ARPE19 treated with 2.5 µM STF-31 for up to 72 hours, showing no adverse effects on ARPE cell morphology or viability. 5 µM STF-31 shows similar results (not shown). (B) Cell viability of H7 hESC, neural progenitor cells (day 10, 12, 14 of differentiation), and ARPE19 treated with 2.5 µM STF-31 for 24 hours. Data expressed as mean+S.D. (n=4); p<0.05,  p<0.01, * p<0.001. (C) Cell viability of PAX6 positive neural progenitor cells treated with STF-31 and nicotinic acid (NA) for 72 hours. Data demonstrate that the cell death observed in neural progenitor cells treated for 72 hours continuously with STF-31 can be rescued with addition of exogenous NA, consistent with the mechanism of NAMPT inhibition observed in the pluripotent stem cells. Data expressed as mean+S.D. (n=4), * p<0.05,  p<0.01, * p<0.001. Altogether, these data demonstrate that short term treatment (24 hours) of the neural progenitor and ARPE cells does not result in significant toxicity.
Figure 11:
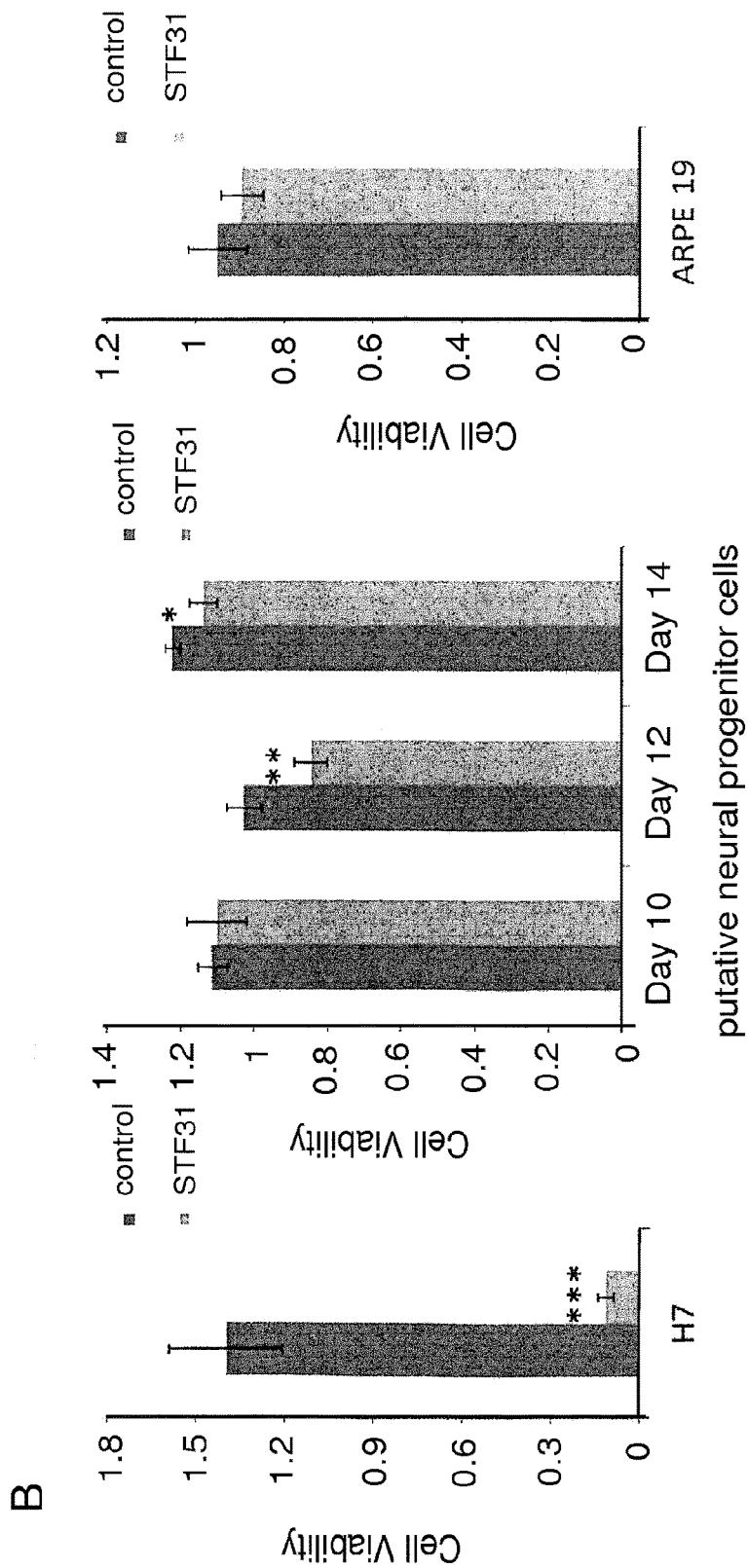
Figure 11:
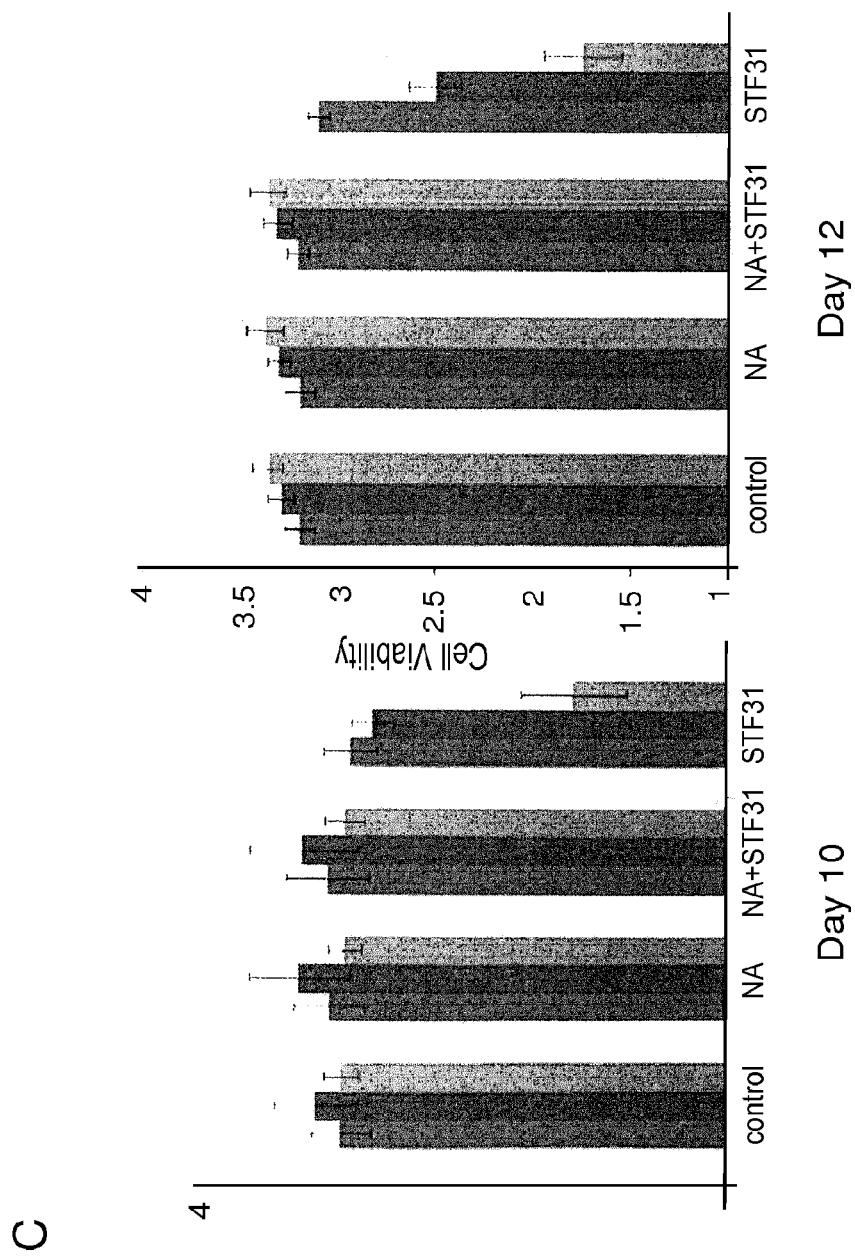

Example 3—STF-31 Spares Human Pluripotent Stem Cell Derived Progeny and Terminally Differentiated Cells Mesenchymal stem cells, fibroblasts, retinal pigmented epithelial cells, human pluripotent stem cell-derived cardiomyocytes, specified hepatic endoderm cells, and neural progenitors show no visible changes in morphology or obvious cell death with STF-31 treatment (FIG. 8A) and viability measurements are consistent with these observations (FIGS. 5A, 5B). Human pluripotent stem cell derived cardiomyocytes and neural progenitor cells treated with STF-31 demonstrate protein and mRNA levels of markers and structural features indistinguishable from controls (FIGS. 8B-C). As shown in FIG. 11, adult pigmented retinal epithelial cells (ARPE) and PAX6 positive neural progenitor cells are also resistant to STF-31 treatment. It was observed that the cell death observed in neural progenitor cells treated for 72 hours continuously with STF-31 can be rescued with addition of exogenous NA, consistent with the mechanism of NAMPT inhibition observed in the pluripotent stem cells. Altogether, these data demonstrate that STF-31 is suitable for a wide range of hPSC derivatives and that short term treatment (24 hours) of the neural progenitors and ARPE cells does not result in significant toxicity.

Example 4—Elimination of Tumorigenic Pluripotent Stem Cell-Derived Progeny in Vitro and In Vivo It is possible that tumors may form from cells that no longer fit the classical functional definition of a pluripotent stem cell. For example, partially differentiated or progenitor cells may self-renew and be tumorigenic, but may not give rise to cells from all three germ layers (thus, precluding them from fitting the functional definition of a true pluripotent cell). In this example, pluripotent stem cell-derived tumorigenic progeny include the following: immature progenitor cells, partially differentiated progeny, fetal-like progeny, non-terminally differentiated progeny, as well as progeny that retain or reactivate pluripotent tumorigenic regulatory pathways and/or tumorigenic characteristics through genetic instability or activation of oncogenic pathways. Here, the compound is used to eliminate neoplasia's initiated from pluripotent stem cell-derived tumorigenic progeny in conjunction with administration of pluripotent stem cell-derived progeny to the mammal (e.g. transplantation of human pluripotent stem cell-derived cardiomyocytes into human). The compound is administered at the same time that the cells or tissue product are delivered, or at a time post-cell delivery (e.g., 1 day to 30 days post-cell injection). The compound may include STF31, FK866, other NAMPT inhibitor, or a combination of NAMPT inhibitors. For example, the compound is administered as a 96 hour continuous infusion every 28 days at recommended dosage of 0.126 mg/m$^2$/h or within the range from 0-0.126 mg/m$^2$/h to prevent the in vivo formation of tumors from the cell or tissue product delivered to the animal. Dosages of FK866 that are non-toxic to humans have been described in Holen et al., *Invest New Drugs* 26(1):45-51 (2008). The progeny to be delivered to the animal may include any pluripotent stem cell derivative (e.g., cardiomyocyte, neuron, hepatocyte, retinal pigmented epithelial cell).

In another embodiment, the compound is used to eliminate or reduce the number of tumorigenic cells from pluripotent stem cell-derived tumorigenic progeny (defined above) in vitro prior to downstream in vitro and in vivo applications. In this method, compound is applied to cell cultures or tissue products for 24-96 hours of treatment time at concentrations ranging from: 0.1-50 µM for STF-31 and 0.001-10 µM for FK866. After treatment for time required to eliminate the tumorigenic population, the compound is removed by multiple washes of appropriate media without compound (e.g., three to five times the volume of culture media) and cells are cultured until utilization in downstream application.

We claim:

1. A method of reducing or eliminating undifferentiated pluripotent stem cells, the method comprising contacting an effective amount of a compound to a heterogeneous cell population or sample comprising or suspected of comprising differentiated cell types and undifferentiated pluripotent stem cells, wherein the compound is a nicotinamide phosphoribosyltransferase (NAMPT) inhibitor, whereby the compound selectively reduces or eliminates undifferentiated pluripotent stem cells from the cell population or sample.

2. The method of claim 1, wherein the NAMPT inhibitor is selected from the group consisting of STF-31, FK866, GMX-1778, GNE-617, and GNE-618.

3. The method of claim 1, wherein the effective amount is an amount between about 1 nanomolar (nM) and about 100 micromolar (µM).

4. The method of claim 3, wherein the compound is STF-31 and the effective amount is about 5 µM.

5. The method of claim 3, wherein the compound is FK866 and the effective amount is about 25 nM.

\* \* \* \* \*